(12) United States Patent
Moses et al.

(10) Patent No.: US 7,811,283 B2
(45) Date of Patent: *Oct. 12, 2010

(54) OPEN VESSEL SEALING INSTRUMENT WITH HOURGLASS CUTTING MECHANISM AND OVER-RATCHET SAFETY

(75) Inventors: Michael C. Moses, Boulder, CO (US); Paul R. Romero, Loveland, CO (US); Kristin D. Johnson, Louisville, CO (US); Duane E. Kerr, Berthoud, CO (US); Sean T. Dycus, Denver, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1283 days.

This patent is subject to a terminal disclaimer.

(21) Appl. No.: 10/962,116

(22) Filed: Oct. 8, 2004

(65) Prior Publication Data

US 2005/0154387 A1 Jul. 14, 2005

Related U.S. Application Data

(63) Continuation-in-part of application No. 10/873,860, filed on Jun. 22, 2004, now Pat. No. 7,252,667.

(60) Provisional application No. 60/523,387, filed on Nov. 19, 2003.

(51) Int. Cl.
*A61B 18/14* (2006.01)
(52) U.S. Cl. .......................... 606/51; 606/46
(58) Field of Classification Search ............. 606/27–52, 606/205–208
See application file for complete search history.

(56) References Cited

U.S. PATENT DOCUMENTS 371,664 A 10/1887 Brannan et al.
(Continued)

FOREIGN PATENT DOCUMENTS

CA 2104423 2/1994
(Continued)

OTHER PUBLICATIONS

Int'l Search Report EP 04 752343.6 dated Jul. 20, 2007.
(Continued)

*Primary Examiner*—Michael Peffley

(57) ABSTRACT

An open electrosurgical forceps for sealing tissue includes a pair of first and second shaft members each having a jaw member disposed at a distal end thereof. The jaw members are movable from a first position in spaced relation relative to one another to at least one subsequent position wherein the jaw members cooperate to grasp tissue therebetween. Each of the jaw members includes an electrically conductive sealing plate for communicating electrosurgical energy through tissue held therebetween. At least one of the jaw members includes a knife channel defined along a length thereof which is dimensioned to reciprocate a cutting blade therealong. An actuator is included which is operatively connected to one of the shaft members and selectively advances the cutting mechanism from a first position wherein the cutting blade is disposed proximal to tissue held between the jaw members to at least one subsequent position wherein the cutting blade is disposed distal to tissue held between the jaw members. The cutting blade is a generally hourglass-shaped flexible cutting blade having a notch disposed generally midway therealong which facilitates distal translation of the knife within the knife channel.

2 Claims, 19 Drawing Sheets

U.S. PATENT DOCUMENTS

| | | |
|---|---|---|
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Xamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |

| | | | | | | |
|---|---|---|---|---|---|---|
| 5,334,183 | A | 8/1994 | Wuchinich | 5,531,744 A | 7/1996 | Nardella et al. |
| 5,334,215 | A | 8/1994 | Chen | 5,536,251 A | 7/1996 | Evard et al. |
| 5,336,220 | A | 8/1994 | Ryan et al. | 5,540,684 A | 7/1996 | Hassler, Jr. |
| 5,336,221 | A | 8/1994 | Anderson | 5,540,685 A | 7/1996 | Parins et al. |
| 5,342,359 | A | 8/1994 | Rydell | 5,540,706 A | 7/1996 | Aust et al. |
| 5,342,381 | A | 8/1994 | Tidemand | 5,540,715 A | 7/1996 | Katsaros et al. |
| 5,342,393 | A | 8/1994 | Stack | 5,542,945 A | 8/1996 | Fritzsch |
| 5,344,424 | A | 9/1994 | Roberts et al. | 5,558,671 A | 9/1996 | Yates |
| 5,350,391 | A | 9/1994 | Iacovelli | 5,558,672 A | 9/1996 | Edwards et al. |
| 5,352,222 | A | 10/1994 | Rydell | 5,562,619 A | 10/1996 | Mirarchi et al. |
| 5,354,271 | A | 10/1994 | Voda | 5,562,699 A | 10/1996 | Heimberger et al. |
| 5,356,408 | A | 10/1994 | Rydell | 5,562,720 A | 10/1996 | Stern et al. |
| 5,366,477 | A | 11/1994 | LeMarie, III et al. | 5,564,615 A | 10/1996 | Bishop et al. |
| 5,368,600 | A | 11/1994 | Failla et al. | 5,569,241 A | 10/1996 | Edwardds |
| 5,374,277 | A | 12/1994 | Hassler | 5,569,243 A | 10/1996 | Kortenbach et al. |
| 5,376,089 | A | 12/1994 | Smith | 5,571,100 A | 11/1996 | Goble et al. |
| 5,383,875 | A | 1/1995 | Bays et al. | 5,573,424 A | 11/1996 | Poppe |
| 5,383,897 | A | 1/1995 | Wholey | 5,573,534 A | 11/1996 | Stone |
| 5,389,098 | A | 2/1995 | Tsuruta et al. | 5,573,535 A | 11/1996 | Viklund |
| 5,389,103 | A | 2/1995 | Melzer et al. | 5,575,799 A | 11/1996 | Bolanos et al. |
| 5,389,104 | A | 2/1995 | Hahnen et al. | 5,575,805 A | 11/1996 | Li |
| 5,391,166 | A | 2/1995 | Eggers | 5,578,052 A | 11/1996 | Koros et al. |
| 5,391,183 | A | 2/1995 | Janzen et al. | 5,579,781 A | 12/1996 | Cooke |
| 5,396,900 | A | 3/1995 | Slater et al. | 5,582,611 A | 12/1996 | Tsuruta et al. |
| 5,403,312 | A | 4/1995 | Yates et al. | 5,582,617 A | 12/1996 | Klieman et al. |
| 5,403,342 | A | 4/1995 | Tovey et al. | 5,585,896 A | 12/1996 | Yamazaki et al. |
| 5,405,344 | A | 4/1995 | Williamson et al. | 5,590,570 A | 1/1997 | LeMaire, III et al. |
| 5,409,763 | A | 4/1995 | Serizawa et al. | 5,591,181 A | 1/1997 | Stone et al. |
| 5,411,519 | A | 5/1995 | Tovey et al. | 5,597,107 A | 1/1997 | Knodel et al. |
| 5,411,520 | A | 5/1995 | Nash et al. | 5,601,224 A | 2/1997 | Bishop et al. |
| 5,413,571 | A | 5/1995 | Katsaros et al. | 5,601,601 A | 2/1997 | Tal et al. |
| 5,415,656 | A | 5/1995 | Tihon et al. | 5,601,641 A | 2/1997 | Stephens |
| 5,415,657 | A | 5/1995 | Taymor-Luria | 5,603,711 A | 2/1997 | Parins et al. |
| 5,422,567 | A | 6/1995 | Matsunaga | 5,603,723 A | 2/1997 | Aranyi et al. |
| 5,423,810 | A | 6/1995 | Goble et al. | 5,611,798 A | 3/1997 | Eggers |
| 5,425,690 | A | 6/1995 | Chang | 5,611,808 A | 3/1997 | Hossain et al. |
| 5,425,739 | A | 6/1995 | Jessen | 5,611,813 A | 3/1997 | Lichtman |
| 5,429,616 | A | 7/1995 | Schaffer | 5,620,415 A | 4/1997 | Lucey et al. |
| 5,431,672 | A | 7/1995 | Cote et al. | 5,620,453 A | 4/1997 | Nallakrishnan |
| 5,431,674 | A | 7/1995 | Basile et al. | 5,620,459 A | 4/1997 | Lichtman |
| 5,437,292 | A | 8/1995 | Kipshidze et al. | 5,624,452 A | 4/1997 | Yates |
| 5,438,302 | A | 8/1995 | Goble | 5,626,578 A | 5/1997 | Tihon |
| 5,439,478 | A | 8/1995 | Palmer | 5,626,609 A | 5/1997 | Zvenyatsky et al. |
| 5,441,517 | A | 8/1995 | Kensey et al. | 5,630,833 A | 5/1997 | Katsaros et al. |
| 5,443,463 | A | 8/1995 | Stern et al. | 5,637,110 A | 6/1997 | Pennybacker et al. |
| 5,443,464 | A | 8/1995 | Russell et al. | 5,638,003 A | 6/1997 | Hall |
| 5,443,480 | A | 8/1995 | Jacobs et al. | 5,643,294 A | 7/1997 | Tovey et al. |
| 5,445,638 | A | 8/1995 | Rydell et al. | 5,647,869 A | 7/1997 | Goble et al. |
| 5,445,658 | A | 8/1995 | Durrfeld et al. | 5,647,871 A | 7/1997 | Levine et al. |
| 5,449,480 | A | 9/1995 | Kuriya et al. | 5,649,959 A | 7/1997 | Hannam et al. |
| 5,451,224 | A | 9/1995 | Goble et al. | 5,655,650 A | 8/1997 | Naitou |
| 5,454,823 | A | 10/1995 | Richardson et al. | 5,658,281 A | 8/1997 | Heard |
| 5,454,827 | A | 10/1995 | Aust et al. | D384,413 S | 9/1997 | Zlock et al. |
| 5,456,684 | A | 10/1995 | Schmidt et al. | 5,662,667 A | 9/1997 | Knodel |
| 5,458,598 | A * | 10/1995 | Feinberg et al. ............... 606/52 | 5,665,100 A | 9/1997 | Yoon |
| 5,460,629 | A | 10/1995 | Shlain et al. | 5,667,526 A | 9/1997 | Levin |
| 5,461,765 | A | 10/1995 | Linden et al. | 5,674,220 A | 10/1997 | Fox et al. |
| 5,462,546 | A | 10/1995 | Rydell | 5,674,229 A | 10/1997 | Tovey et al. |
| 5,472,442 | A | 12/1995 | Klicek | 5,681,282 A | 10/1997 | Eggers et al. |
| 5,472,443 | A | 12/1995 | Cordis et al. | 5,688,270 A | 11/1997 | Yates et al. |
| 5,478,351 | A | 12/1995 | Meade et al. | 5,690,652 A | 11/1997 | Wurster et al. |
| 5,480,406 | A | 1/1996 | Nolan et al. | 5,690,653 A | 11/1997 | Richardson et al. |
| 5,480,409 | A | 1/1996 | Riza | 5,693,051 A * | 12/1997 | Schulze et al. ............... 606/51 |
| 5,484,436 | A | 1/1996 | Eggers et al. | 5,693,920 A | 12/1997 | Maeda |
| 5,496,312 | A | 3/1996 | Klicek | 5,695,522 A | 12/1997 | LeMaire, III et al. |
| 5,496,317 | A | 3/1996 | Goble et al. | 5,700,261 A | 12/1997 | Brinkerhoff |
| 5,496,347 | A | 3/1996 | Hashiguchi et al. | 5,700,270 A | 12/1997 | Peyser et al. |
| 5,499,997 | A | 3/1996 | Sharpe et al. | 5,702,390 A | 12/1997 | Austin et al. |
| 5,509,922 | A | 4/1996 | Aranyi et al. | 5,707,369 A | 1/1998 | Vaitekunas et al. |
| 5,514,134 | A | 5/1996 | Rydell et al. | 5,709,680 A | 1/1998 | Yates et al. |
| 5,527,313 | A | 6/1996 | Scott et al. | 5,716,366 A | 2/1998 | Yates |
| 5,528,833 | A | 6/1996 | Sakuma | 5,720,744 A | 2/1998 | Eggleston et al. |
| 5,529,067 | A | 6/1996 | Larsen et al. | 5,722,421 A | 3/1998 | Francese et al. |

| | | | | | | |
|---|---|---|---|---|---|---|
| 5,725,536 | A | * | 3/1998 | Oberlin et al. ............... 606/139 | | |
| 5,727,428 | A | | 3/1998 | LeMaire, III et al. | | |
| 5,735,848 | A | | 4/1998 | Yates et al. | | |
| 5,743,906 | A | | 4/1998 | Parins et al. | | |
| 5,752,973 | A | | 5/1998 | Kieturakis | | |
| 5,755,717 | A | | 5/1998 | Yates et al. | | |
| 5,759,188 | A | | 6/1998 | Yoon | | |
| 5,766,130 | A | | 6/1998 | Selmonosky | | |
| 5,766,166 | A | | 6/1998 | Hooven | | |
| 5,766,170 | A | | 6/1998 | Eggers | | |
| 5,766,196 | A | | 6/1998 | Griffiths | | |
| 5,769,849 | A | | 6/1998 | Eggers | | |
| 5,772,655 | A | | 6/1998 | Bauer et al. | | |
| 5,772,670 | A | | 6/1998 | Brosa | | |
| 5,776,128 | A | | 7/1998 | Eggers | | |
| 5,776,130 | A | | 7/1998 | Buysse et al. | | |
| 5,779,646 | A | | 7/1998 | Koblish et al. | | |
| 5,779,701 | A | | 7/1998 | McBrayer et al. | | |
| H1745 | H | | 8/1998 | Paraschac | | |
| 5,792,137 | A | | 8/1998 | Carr et al. | | |
| 5,792,165 | A | | 8/1998 | Klieman et al. | | |
| 5,792,177 | A | | 8/1998 | Kaseda | | |
| 5,797,537 | A | | 8/1998 | Oberlin et al. | | |
| 5,797,927 | A | | 8/1998 | Yoon | | |
| 5,797,938 | A | | 8/1998 | Paraschac et al. | | |
| 5,797,941 | A | | 8/1998 | Schulze et al. | | |
| 5,797,958 | A | | 8/1998 | Yoon | | |
| 5,800,449 | A | | 9/1998 | Wales | | |
| 5,807,393 | A | | 9/1998 | Williamsom, IV et al. | | |
| 5,810,764 | A | | 9/1998 | Eggers et al. | | |
| 5,810,805 | A | | 9/1998 | Sutcu et al. | | |
| 5,810,808 | A | | 9/1998 | Eggers | | |
| 5,810,811 | A | | 9/1998 | Yates et al. | | |
| 5,810,877 | A | | 9/1998 | Roth et al. | | |
| 5,814,043 | A | | 9/1998 | Shapeton | | |
| 5,814,054 | A | | 9/1998 | Kortenbach et al. | | |
| 5,817,093 | A | | 10/1998 | Williamson, IV et al. | | |
| 5,817,119 | A | | 10/1998 | Klieman et al. | | |
| 5,820,630 | A | | 10/1998 | Lind | | |
| 5,824,978 | A | | 10/1998 | Karasik et al. | | |
| 5,827,271 | A | | 10/1998 | Buysse et al. | | |
| 5,827,279 | A | * | 10/1998 | Hughett et al. ................. 606/45 | | |
| 5,827,281 | A | | 10/1998 | Levin | | |
| 5,827,323 | A | | 10/1998 | Klieman et al. | | |
| 5,827,548 | A | | 10/1998 | Lavallee et al. | | |
| 5,833,690 | A | | 11/1998 | Yates et al. | | |
| 5,843,080 | A | | 12/1998 | Fleenor et al. | | |
| 5,849,022 | A | | 12/1998 | Sakashita et al. | | |
| 5,853,412 | A | | 12/1998 | Mayenberger | | |
| 5,859,527 | A | | 1/1999 | Cook | | |
| 5,860,976 | A | | 1/1999 | Billings et al. | | |
| 5,876,401 | A | | 3/1999 | Schulze et al. | | |
| 5,876,412 | A | | 3/1999 | Piraka | | |
| 5,882,567 | A | | 3/1999 | Cavallaro et al. | | |
| 5,891,141 | A | | 4/1999 | Rydell | | |
| 5,891,142 | A | | 4/1999 | Eggers et al. | | |
| 5,893,863 | A | | 4/1999 | Yoon | | |
| 5,893,875 | A | | 4/1999 | O'Connor et al. | | |
| 5,893,877 | A | | 4/1999 | Gampp, Jr. et al. | | |
| 5,897,563 | A | | 4/1999 | Yoon et al. | | |
| 5,902,301 | A | | 5/1999 | Olig | | |
| 5,906,630 | A | | 5/1999 | Anderhub et al. | | |
| 5,908,420 | A | | 6/1999 | Parins et al. | | |
| 5,908,432 | A | | 6/1999 | Pan | | |
| 5,911,719 | A | | 6/1999 | Eggers | | |
| 5,913,874 | A | | 6/1999 | Berns et al. | | |
| 5,921,916 | A | | 7/1999 | Aeikens et al. | | |
| 5,921,984 | A | | 7/1999 | Sutcu et al. | | |
| 5,925,043 | A | | 7/1999 | Kumar et al. | | |
| 5,928,136 | A | | 7/1999 | Barry | | |
| 5,935,126 | A | | 8/1999 | Riza | | |
| 5,941,869 | A | | 8/1999 | Patterson et al. | | |
| 5,944,718 | A | | 8/1999 | Austin et al. | | |
| 5,951,546 | A | | 9/1999 | Lorentzen | | |
| 5,951,549 | A | | 9/1999 | Richardson et al. | | |
| 5,954,720 | A | | 9/1999 | Wilson et al. | | |
| 5,954,731 | A | | 9/1999 | Yoon | | |
| 5,954,733 | A | | 9/1999 | Yoon | | |
| 5,957,923 | A | | 9/1999 | Hahnen et al. | | |
| 5,957,937 | A | | 9/1999 | Yoon | | |
| 5,960,544 | A | | 10/1999 | Beyers | | |
| 5,961,514 | A | | 10/1999 | Long et al. | | |
| 5,964,758 | A | | 10/1999 | Dresden | | |
| 5,976,132 | A | | 11/1999 | Morris | | |
| 5,984,932 | A | | 11/1999 | Yoon | | |
| 5,984,938 | A | | 11/1999 | Yoon | | |
| 5,984,939 | A | | 11/1999 | Yoon | | |
| 5,989,277 | A | | 11/1999 | LeMaire, III et al. | | |
| 5,993,466 | A | | 11/1999 | Yoon | | |
| 5,993,467 | A | | 11/1999 | Yoon | | |
| 5,997,565 | A | | 12/1999 | Inoue | | |
| 6,004,332 | A | | 12/1999 | Yoon et al. | | |
| 6,004,335 | A | | 12/1999 | Vaitekunas et al. | | |
| 6,010,516 | A | | 1/2000 | Hulka | | |
| 6,017,358 | A | | 1/2000 | Yoon et al. | | |
| 6,021,693 | A | | 2/2000 | Feng-Sing | | |
| 6,024,741 | A | | 2/2000 | Willaimson et al. | | |
| 6,024,743 | A | | 2/2000 | Edwards | | |
| 6,024,744 | A | | 2/2000 | Kese et al. | | |
| 6,027,522 | A | | 2/2000 | Palmer | | |
| 6,030,384 | A | | 2/2000 | Nezhat | | |
| 6,033,399 | A | | 3/2000 | Gines | | |
| 6,039,733 | A | | 3/2000 | Buysse et al. | | |
| 6,041,679 | A | | 3/2000 | Slater et al. | | |
| 6,050,996 | A | | 4/2000 | Schmaltz et al. | | |
| 6,053,914 | A | | 4/2000 | Eggers et al. | | |
| 6,053,933 | A | | 4/2000 | Balazs et al. | | |
| D424,694 | S | | 5/2000 | Tetzlaff et al. | | |
| D425,201 | S | | 5/2000 | Tetzlaff et al. | | |
| 6,059,782 | A | | 5/2000 | Novak et al. | | |
| 6,066,139 | A | | 5/2000 | Ryan et al. | | |
| 6,074,386 | A | | 6/2000 | Goble et al. | | |
| 6,077,287 | A | | 6/2000 | Taylor et al. | | |
| 6,080,180 | A | | 6/2000 | Yoon et al. | | |
| RE36,795 | E | | 7/2000 | Rydell | | |
| 6,083,223 | A | | 7/2000 | Baker | | |
| 6,086,586 | A | | 7/2000 | Hooven | | |
| 6,086,601 | A | | 7/2000 | Yoon | | |
| 6,090,107 | A | | 7/2000 | Borgmeier et al. | | |
| 6,096,037 | A | | 8/2000 | Mulier et al. | | |
| 6,099,550 | A | | 8/2000 | Yoon | | |
| 6,102,909 | A | | 8/2000 | Chen et al. | | |
| 6,106,542 | A | | 8/2000 | Toybin et al. | | |
| 6,110,171 | A | | 8/2000 | Rydell | | |
| 6,113,596 | A | | 9/2000 | Hooven et al. | | |
| 6,113,598 | A | | 9/2000 | Baker | | |
| 6,117,158 | A | | 9/2000 | Measamer et al. | | |
| 6,122,549 | A | | 9/2000 | Sharkey et al. | | |
| 6,123,701 | A | | 9/2000 | Nezhat | | |
| H1904 | H | | 10/2000 | Yates et al. | | |
| 6,126,658 | A | | 10/2000 | Baker | | |
| 6,126,665 | A | | 10/2000 | Yoon | | |
| 6,139,563 | A | | 10/2000 | Cosgrove, III et al. | | |
| 6,143,005 | A | | 11/2000 | Yoon et al. | | |
| 6,152,923 | A | | 11/2000 | Ryan | | |
| 6,162,220 | A | | 12/2000 | Nezhat | | |
| 6,171,316 | B1 | | 1/2001 | Kovac et al. | | |
| 6,174,309 | B1 | | 1/2001 | Wrublewski et al. | | |
| 6,178,628 | B1 | | 1/2001 | Clemens et al. | | |
| 6,179,834 | B1 | | 1/2001 | Buysse et al. | | |
| 6,179,837 | B1 | | 1/2001 | Hooven | | |
| 6,183,467 | B1 | | 2/2001 | Shapeton et al. | | |
| 6,187,003 | B1 | | 2/2001 | Buysse et al. | | |
| 6,190,386 | B1 | | 2/2001 | Rydell | | |
| 6,190,400 | B1 | | 2/2001 | VanDeMoer et al. | | |
| 6,193,718 | B1 | | 2/2001 | Kortenbach et al. | | |

| Patent No. | Date | Inventor |
|---|---|---|
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B2 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |

| | | | | | | |
|---|---|---|---|---|---|---|
| 6,934,134 B2 | 8/2005 | Mori et al. | 7,241,296 B2 | 7/2007 | Buysse et al. | |
| 6,936,061 B2 | 8/2005 | Sasaki | 7,244,257 B2 | 7/2007 | Podjahsky et al. | |
| D509,297 S | 9/2005 | Wells | 7,246,734 B2 | 7/2007 | Shelto, IV | |
| 6,942,662 B2 | 9/2005 | Goble et al. | 7,248,944 B2 | 7/2007 | Green | |
| 6,943,311 B2 | 9/2005 | Miyako | 7,252,667 B2 * | 8/2007 | Moses et al. | 606/51 |
| 6,953,430 B2 | 10/2005 | Kodooka | 7,255,697 B2 | 8/2007 | Dycus et al. | |
| 6,953,461 B2 | 10/2005 | McClurken et al. | 7,267,677 B2 | 9/2007 | Johnson et al. | |
| 6,958,070 B2 | 10/2005 | Witt et al. | 7,270,660 B2 | 9/2007 | Ryan | |
| 6,960,210 B2 | 11/2005 | Lands et al. | 7,270,664 B2 | 9/2007 | Johnson et al. | |
| 6,964,662 B2 | 11/2005 | Kidooka | 7,276,068 B2 | 10/2007 | Johnson et al. | |
| 6,966,907 B2 | 11/2005 | Goble | 7,300,435 B2 | 11/2007 | Wham et al. | |
| 6,972,017 B2 | 12/2005 | Smith et al. | 7,303,557 B2 | 12/2007 | Wham et al. | |
| 6,977,495 B2 | 12/2005 | Donofrio | 7,311,709 B2 | 12/2007 | Truckai et al. | |
| 6,979,786 B2 | 12/2005 | Aukland et al. | 7,314,471 B2 | 1/2008 | Holman | |
| 6,981,628 B2 | 1/2006 | Wales | 7,318,823 B2 | 1/2008 | Sharps et al. | |
| 6,987,244 B2 | 1/2006 | Bauer | 7,329,256 B2 | 2/2008 | Johnson et al. | |
| 6,994,707 B2 | 2/2006 | Ellman et al. | 7,329,257 B2 | 2/2008 | Kanehira et al. | |
| 6,994,709 B2 | 2/2006 | Iida | D564,662 S | 3/2008 | Moses et al. | |
| 6,997,931 B2 | 2/2006 | Sauer et al. | 7,338,526 B2 | 3/2008 | Steinberg | |
| 7,001,381 B2 | 2/2006 | Harano et al. | 7,342,754 B2 | 3/2008 | Fitzgerald et al. | |
| 7,011,657 B2 | 3/2006 | Truckai et al. | 7,344,268 B2 | 3/2008 | Jigamian | |
| 7,033,354 B2 | 4/2006 | Keppel | D567,943 S | 4/2008 | Moses et al. | |
| 7,033,356 B2 | 4/2006 | Latterell et al. | 7,367,976 B2 | 5/2008 | Lawes et al. | |
| 7,041,102 B2 | 5/2006 | Truckai et al. | 7,377,920 B2 | 5/2008 | Buysse et al. | |
| 7,044,948 B2 | 5/2006 | Keppel | 7,384,420 B2 | 6/2008 | Dycus et al. | |
| 7,052,489 B2 | 5/2006 | Griego et al. | 7,384,421 B2 | 6/2008 | Hushka | |
| 7,052,496 B2 | 5/2006 | Yamauchi | 7,396,336 B2 | 7/2008 | Orszulak et al. | |
| 7,063,715 B2 | 6/2006 | Onuki et al. | D575,395 S | 8/2008 | Hushka | |
| D525,361 S | 7/2006 | Hushka | D575,401 S | 8/2008 | Hixson et al. | |
| 7,070,597 B2 | 7/2006 | Truckai et al. | 7,435,249 B2 | 10/2008 | Buysse et al. | |
| 7,083,618 B2 | 8/2006 | Couture et al. | 7,442,193 B2 | 10/2008 | Shields et al. | |
| 7,083,619 B2 | 8/2006 | Truckai et al. | 7,442,194 B2 | 10/2008 | Dumbauld et al. | |
| 7,083,620 B2 | 8/2006 | Jahns et al. | 7,445,621 B2 | 11/2008 | Dumbauld et al. | |
| 7,087,051 B2 | 8/2006 | Bourne et al. | 7,458,972 B2 | 12/2008 | Keppel | |
| 7,087,054 B2 | 8/2006 | Truckai et al. | 7,473,253 B2 | 1/2009 | Dycus et al. | |
| 7,090,673 B2 | 8/2006 | Dycus et al. | 7,481,810 B2 | 1/2009 | Dumbauld et al. | |
| 7,090,689 B2 | 8/2006 | Nagase et al. | 7,487,780 B2 | 2/2009 | Hooven | |
| 7,101,371 B2 | 9/2006 | Dycus et al. | 7,491,201 B2 | 2/2009 | Shields et al. | |
| 7,101,372 B2 | 9/2006 | Dycus et al. | 7,491,202 B2 | 2/2009 | Odom et al. | |
| 7,101,373 B2 | 9/2006 | Dycus et al. | 7,500,975 B2 | 3/2009 | Cunningham et al. | |
| 7,103,947 B2 | 9/2006 | Sartor et al. | 7,510,556 B2 | 3/2009 | Nguyen et al. | |
| 7,107,124 B2 | 9/2006 | Green | 7,513,898 B2 | 4/2009 | Johnson et al. | |
| 7,112,199 B2 | 9/2006 | Cosmescu | 7,540,872 B2 | 6/2009 | Schechter et al. | |
| D531,311 S | 10/2006 | Guerra et al. | 7,549,995 B2 | 6/2009 | Schultz | |
| 7,115,123 B2 | 10/2006 | Knowlton et al. | 7,553,312 B2 | 6/2009 | Tetzlaff et al. | |
| 7,118,570 B2 | 10/2006 | Tetzlaff et al. | 2002/0013583 A1 | 1/2002 | Camran et al. | |
| 7,118,587 B2 | 10/2006 | Dycus et al. | 2002/0049442 A1 | 4/2002 | Roberts et al. | |
| 7,131,860 B2 | 11/2006 | Sartor et al. | 2002/0099372 A1 | 7/2002 | Schulze et al. | |
| 7,131,970 B2 * | 11/2006 | Moses et al. ............... 606/51 | 2002/0107517 A1 | 8/2002 | Witt et al. | |
| 7,131,971 B2 | 11/2006 | Dycus et al. | 2002/0111624 A1 | 8/2002 | Witt et al. | |
| 7,135,020 B2 | 11/2006 | Lawes et al. | 2002/0188294 A1 | 12/2002 | Couture et al. | |
| D533,942 S | 12/2006 | Kerr et al. | 2003/0014052 A1 | 1/2003 | Buysse et al. | |
| 7,145,757 B2 | 12/2006 | Shea et al. | 2003/0014053 A1 | 1/2003 | Nguyen et al. | |
| 7,147,638 B2 | 12/2006 | Chapman et al. | 2003/0018331 A1 | 1/2003 | Dycus et al. | |
| 7,150,097 B2 | 12/2006 | Sremcich et al. | 2003/0018332 A1 | 1/2003 | Schmaltz et al. | |
| 7,150,749 B2 | 12/2006 | Dycus et al. | 2003/0032956 A1 | 2/2003 | Lands et al. | |
| 7,153,314 B2 | 12/2006 | Laufer et al. | 2003/0069570 A1 | 4/2003 | Witzel et al. | |
| D535,027 S | 1/2007 | James et al. | 2003/0069571 A1 | 4/2003 | Treat et al. | |
| 7,156,842 B2 | 1/2007 | Sartor et al. | 2003/0078578 A1 | 4/2003 | Truckai et al. | |
| 7,156,846 B2 | 1/2007 | Dycus et al. | 2003/0109875 A1 | 6/2003 | Tetzlaff et al. | |
| 7,160,298 B2 | 1/2007 | Lawes et al. | 2003/0114851 A1 | 6/2003 | Truckai et al. | |
| 7,160,299 B2 | 1/2007 | Baily | 2003/0139741 A1 | 7/2003 | Goble et al. | |
| 7,169,146 B2 | 1/2007 | Truckai et al. | 2003/0139742 A1 | 7/2003 | Wampler et al. | |
| 7,179,255 B2 | 2/2007 | Lettice et al. | 2003/0158548 A1 | 8/2003 | Phan et al. | |
| 7,179,256 B2 | 2/2007 | Buysse et al. | 2003/0158549 A1 | 8/2003 | Swanson | |
| 7,195,631 B2 | 3/2007 | Dumbauld | 2003/0171747 A1 | 9/2003 | Kanehira et al. | |
| D541,418 S | 4/2007 | Schechter et al. | 2003/0181910 A1 | 9/2003 | Dycus et al. | |
| 7,207,990 B2 | 4/2007 | Lands et al. | 2003/0199869 A1 | 10/2003 | Johnson et al. | |
| D541,938 S | 5/2007 | Kerr et al. | 2003/0216732 A1 | 11/2003 | Truckai et al. | |
| 7,223,264 B2 | 5/2007 | Daniel et al. | 2003/0220637 A1 | 11/2003 | Truckai et al. | |
| 7,223,265 B2 | 5/2007 | Keppel | 2003/0229344 A1 | 12/2003 | Dycus et al. | |
| 7,232,440 B2 | 6/2007 | Dumbauld et al. | 2003/0236325 A1 | 12/2003 | Bonora | |
| 7,241,288 B2 | 7/2007 | Braun | 2003/0236518 A1 | 12/2003 | Marchitto et al. | |

| | | |
|---|---|---|
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0176762 A1 | 9/2004 | Lawes et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004569 A1 | 1/2005 | Witt et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |

| | | | | | | |
|---|---|---|---|---|---|---|
| 2009/0048596 | A1 | 2/2009 | Shields et al. | EP | 1177771 | 2/2002 |
| 2009/0062794 | A1 | 3/2009 | Buysse et al. | EP | 1301135 A | 4/2003 |
| 2009/0082766 | A1 | 3/2009 | Unger et al. | EP | 1330991 A1 | 7/2003 |
| 2009/0082767 | A1 | 3/2009 | Unger et al. | EP | 1486177 A2 | 6/2004 |
| 2009/0082769 | A1 | 3/2009 | Unger et al. | EP | 1472984 A1 | 11/2004 |
| 2009/0088738 | A1 | 4/2009 | Guerra et al. | EP | 0774232 | 1/2005 |
| 2009/0088739 | A1 | 4/2009 | Hushka et al. | EP | 1527747 A2 | 5/2005 |
| 2009/0088740 | A1 | 4/2009 | Guerra et al. | EP | 1530952 A1 | 5/2005 |
| 2009/0088741 | A1 | 4/2009 | Hushka et al. | EP | 1532932 A1 | 5/2005 |
| 2009/0088744 | A1 | 4/2009 | Townsend | EP | 1535581 A2 | 6/2005 |
| 2009/0088745 | A1 | 4/2009 | Hushka et al. | EP | 1609430 A1 | 12/2005 |
| 2009/0088746 | A1 | 4/2009 | Hushka et al. | EP | 1632192 A1 | 3/2006 |
| 2009/0088747 | A1 | 4/2009 | Hushka et al. | EP | 1642543 | 4/2006 |
| 2009/0088748 | A1 | 4/2009 | Guerra et al. | EP | 1645238 A1 | 4/2006 |
| 2009/0088749 | A1 | 4/2009 | Hushka et al. | EP | 1645240 A2 | 4/2006 |
| 2009/0088750 | A1 | 4/2009 | Hushka et al. | EP | 1649821 | 4/2006 |
| 2009/0112206 | A1 | 4/2009 | Dumbauld et al. | EP | 1707143 A1 | 10/2006 |
| 2009/0131934 | A1 | 5/2009 | Odom et al. | EP | 1769765 | 4/2007 |
| 2009/0149853 | A1 | 6/2009 | Shields et al. | EP | 1769766 | 4/2007 |
| 2009/0149854 | A1 | 6/2009 | Cunningham et al. | EP | 1929970 | 6/2008 |
| 2009/0171350 | A1 | 7/2009 | Dycus et al. | EP | 1683496 | 12/2008 |
| 2009/0171353 | A1 | 7/2009 | Johnson et al. | GB | 623316 | 5/1949 |
| 2009/0182327 | A1 | 7/2009 | Unger | GB | 1490585 | 11/1977 |
| 2009/0187188 | A1 | 7/2009 | Guerra et al. | GB | 2214430 A | 6/1989 |
| | | | | GB | 2213416 | 8/1989 |

FOREIGN PATENT DOCUMENTS

| | | | | | |
|---|---|---|---|---|---|
| | | | JP | 501068 | 9/1984 |
| DE | 2415263 | 10/1975 | JP | 502328 | 3/1992 |
| DE | 2514501 | 10/1976 | JP | 5-5106 | 1/1993 |
| DE | 2627679 | 1/1977 | JP | 5-40112 | 2/1993 |
| DE | 3612646 | 4/1987 | JP | 06343644 A2 | 12/1994 |
| DE | 8712328 | 3/1988 | JP | 07265328 A2 | 10/1995 |
| DE | 4303882 | 8/1994 | JP | 08056955 A2 | 3/1996 |
| DE | 4403252 | 8/1995 | JP | 08252263 A2 | 10/1996 |
| DE | 19515914 | 7/1996 | JP | 09010223 A2 | 1/1997 |
| DE | 29616210 | 1/1997 | JP | 11244298 A2 | 9/1999 |
| DE | 19608716 | 4/1997 | JP | 2000342599 A2 | 12/2000 |
| DE | 19751106 | 5/1998 | JP | 2000350732 A2 | 12/2000 |
| DE | 19751108 | 5/1999 | JP | 2001008944 A2 | 1/2001 |
| DE | 19738457 | 1/2009 | JP | 2001029356 A2 | 2/2001 |
| EP | 0364216 A1 | 4/1990 | JP | 2001128990 A2 | 5/2001 |
| EP | 0467501 | 1/1992 | SU | 401367 | 11/1974 |
| EP | 0518230 A1 | 12/1992 | WO | WO89/00757 | 1/1989 |
| EP | 0 541 930 B1 | 5/1993 | WO | WO 92/04873 | 4/1992 |
| EP | 0572131 | 12/1993 | WO | WO 92/06642 | 4/1992 |
| EP | 0584787 A1 | 3/1994 | WO | WO 93/21845 | 11/1993 |
| EP | 0589453 A2 | 3/1994 | WO | WO 94/08524 A | 4/1994 |
| EP | 0589555 | 3/1994 | WO | WO94/20025 | 9/1994 |
| EP | 0623316 A1 | 11/1994 | WO | WO 95/02369 | 1/1995 |
| EP | 0624348 A2 | 11/1994 | WO | WO95/07662 | 3/1995 |
| EP | 0650701 A1 | 5/1995 | WO | WO 95/07662 | 3/1995 |
| EP | 0694290 A3 | 3/1996 | WO | WO95/15124 | 6/1995 |
| EP | 0717966 A1 | 6/1996 | WO | WO96/05776 | 2/1996 |
| EP | 0754437 A3 | 3/1997 | WO | WO 96/22056 | 7/1996 |
| EP | 0517243 | 9/1997 | WO | WO 96/13218 | 9/1996 |
| EP | 0853922 A1 | 7/1998 | WO | WO 97/00646 | 1/1997 |
| EP | 0875209 A1 | 11/1998 | WO | WO 97/00647 | 1/1997 |
| EP | 0878169 A1 | 11/1998 | WO | WO97/10764 | 3/1997 |
| EP | 0887046 A3 | 1/1999 | WO | WO 97/10764 | 3/1997 |
| EP | 0923907 A1 | 6/1999 | WO | WO 97/24073 | 7/1997 |
| EP | 0986990 A1 | 3/2000 | WO | WO 97/24993 | 7/1997 |
| EP | 1034747 A1 | 9/2000 | WO | WO 98/27880 | 7/1998 |
| EP | 1034748 A1 | 9/2000 | WO | WO 99/03407 | 1/1999 |
| EP | 1025807 A3 | 10/2000 | WO | WO 99/03408 | 1/1999 |
| EP | 1034746 A3 | 10/2000 | WO | WO 99/03409 | 1/1999 |
| EP | 1050278 A1 | 11/2000 | WO | WO 99/12488 | 3/1999 |
| EP | 1053719 A1 | 11/2000 | WO | WO 99/12488 A | 3/1999 |
| EP | 1053720 A1 | 11/2000 | WO | WO 99/23933 | 5/1999 |
| EP | 1055399 A1 | 11/2000 | WO | WO 99/40857 | 8/1999 |
| EP | 1055400 A1 | 11/2000 | WO | WO 99/40861 | 8/1999 |
| EP | 1080694 A1 | 3/2001 | WO | WO 99/51158 | 10/1999 |
| EP | 1082944 A1 | 3/2001 | WO | WO 99/66850 | 12/1999 |
| EP | 1159926 A2 | 12/2001 | WO | WO 99/66850 A | 12/1999 |
| | | | WO | WO 00/24330 | 5/2000 |

| | | |
|---|---|---|
| WO | WO 00/24331 | 5/2000 |
| WO | WO00/24331 | 5/2000 |
| WO | WO 00/36986 | 6/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO02/07627 | 1/2002 |
| WO | WO 02/07627 | 1/2002 |
| WO | WO 02/067798 A1 | 9/2002 |
| WO | WO 02/080783 | 10/2002 |
| WO | WO02/080783 | 10/2002 |
| WO | WO02/080784 | 10/2002 |
| WO | WO 02/080784 | 10/2002 |
| WO | WO02/080785 | 10/2002 |
| WO | WO 02/080785 | 10/2002 |
| WO | WO 02/080786 | 10/2002 |
| WO | WO02/080786 | 10/2002 |
| WO | WO02/080793 | 10/2002 |
| WO | WO 02/080793 | 10/2002 |
| WO | WO02/080794 | 10/2002 |
| WO | WO 02/080794 | 10/2002 |
| WO | WO 02/080795 | 10/2002 |
| WO | WO 02/080796 | 10/2002 |
| WO | WO 02/080796 A1 | 10/2002 |
| WO | WO02/080797 | 10/2002 |
| WO | WO 02/080797 | 10/2002 |
| WO | WO 02/080798 | 10/2002 |
| WO | WO 02/080798 A1 | 10/2002 |
| WO | WO 02/080799 | 10/2002 |
| WO | WO 02/081170 | 10/2002 |
| WO | WO02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO2004/032777 | 4/2004 |
| WO | WO 2004/032777 | 4/2004 |
| WO | WO 2004/052221 A1 | 6/2004 |
| WO | WO 2004/073488 A2 | 9/2004 |
| WO | WO2004/073490 | 9/2004 |
| WO | WO 2004/073490 | 9/2004 |
| WO | WO2004/073753 | 9/2004 |
| WO | WO 2004/082495 | 9/2004 |
| WO | WO 2004/082495 A1 | 9/2004 |
| WO | WO 2004/098383 A1 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan. 2004.
Johnson et al. "Evaluation of a Bipolar electrothermal Vessel Sealing Device in Hemorrhoidectomy" Sales Product Literature; Jan. 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
PCT/US01/11340, International Search Report.
PCT/US01/11420, International Search Report.
PCT/US02/01890, International Search Report.
PCT/US02/11100, International Search Report.
PCT/USO4/03436, International Search Report.
PCT/US04/13273, International Search Report.
PCT/US04/15311, International Search Report.
EP 98944778, International Search Report.
EP 98958575, International Search Report.
EP 04027479, International Search Report.
EP 04027705, International Search Report.
EP 04027314, International Search Report.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 878-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature.

LigaSure Vessel Sealing System, the Seal of Confidence in General, Gynecologic, Urologic, and Laparaoscopic Surgery Sales/Product Literature.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC.

"Reducing Needlestick Injuries in the Operating Room" Sales/Product Literature.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery. vol. 181, No. 3, Apr. 2001 pp. 236-237.

W. Scott Helton, "LigaSure Vessel Sealing System: Revolutionary Hemostasis Product for General Surgery" Sales/Product Literature.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.

Muller et al., "Extended Left Hemicolectomy Using the LigaSure Vessel Sealing System" Innovations That Work, Sep. 1999.

Herman et al., "Laparoscopic Intestinal Resection With the LigaSure Vessel Sealing System: A Case Report" Innovations That Work, Feb. 2002.

Carus et al., "Initial Experience With The LigaSure Vessel Sealing System in Abdominal Surgery" Innovations That Work, Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing for Hemostasis During Gynecologic Surgery" Sales/Product Literature.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson et al. "Radical Cystectomy in Females" Current Surgical Techniques in Urology, vol. 14, Issue 3.

E. David Crawford "Use of a Novel Vessel Sealing Technology in Management of the Dorsal Veinous Complex" Sales/Product Literature.

Jarrett et al., "Use of the LigaSure Vessel Sealing System for Peri-Hilar Vessels in Laparoscopic Nephrectomy" Sales/Product Literature.

E. David Crawford "Evaluation of a New Vessel Sealing Device in Urologic Cancer Surgery" Sales/Product Literature.

Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.

Dulemba et al. "Use of a Bipolar Electrothermal Vessel Sealer in Laparoscopically Assisted Vaginal Hysterectomy" Sales/Product Literature.

Johnson et al. "Evaluation of a Bipolar electrothermal Vessel Sealing Device in Hemorrhoidectomy" Sales/Product Literature.

Int'l Search Report PCT/US01/11218.
Int'l Search Report PCT/US99/24869.
Int'l Search Report PCT/US98/18640.
Int'l Search Report PCT/US98/23950.
Int'l Search Report PCT/US04/13273.
Int'l Search Report PCT/US04/15311.
Int'l Search Report PCT/US01/11420.
Int'l Search Report PCT/US02/11100.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Crouch et al. "A Velocity-Dependent Model for Needle Insertion in Soft Tissue" MICCAI 2005; LNCS 3750 pp. 624-632, Dated: 2005.

Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

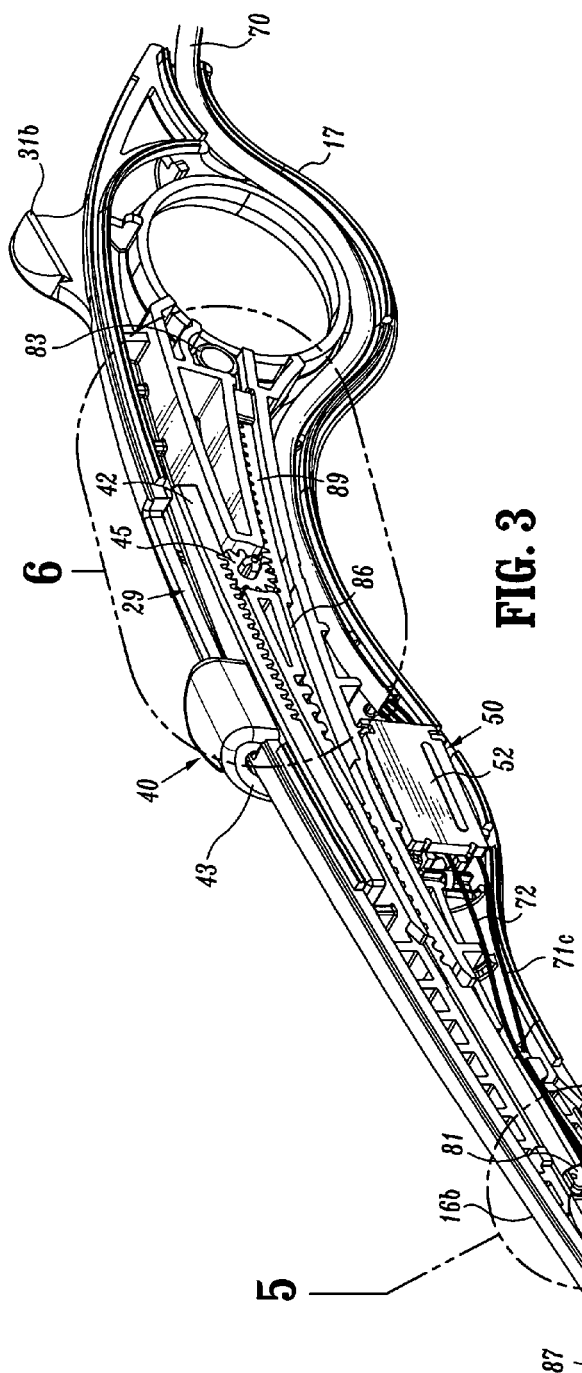
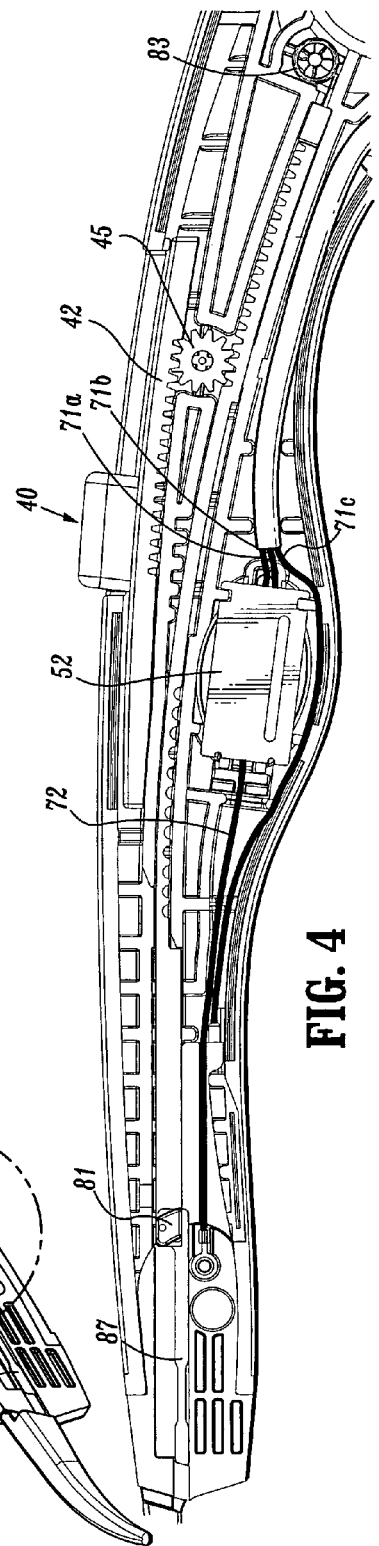
FIG. 3
FIG. 4

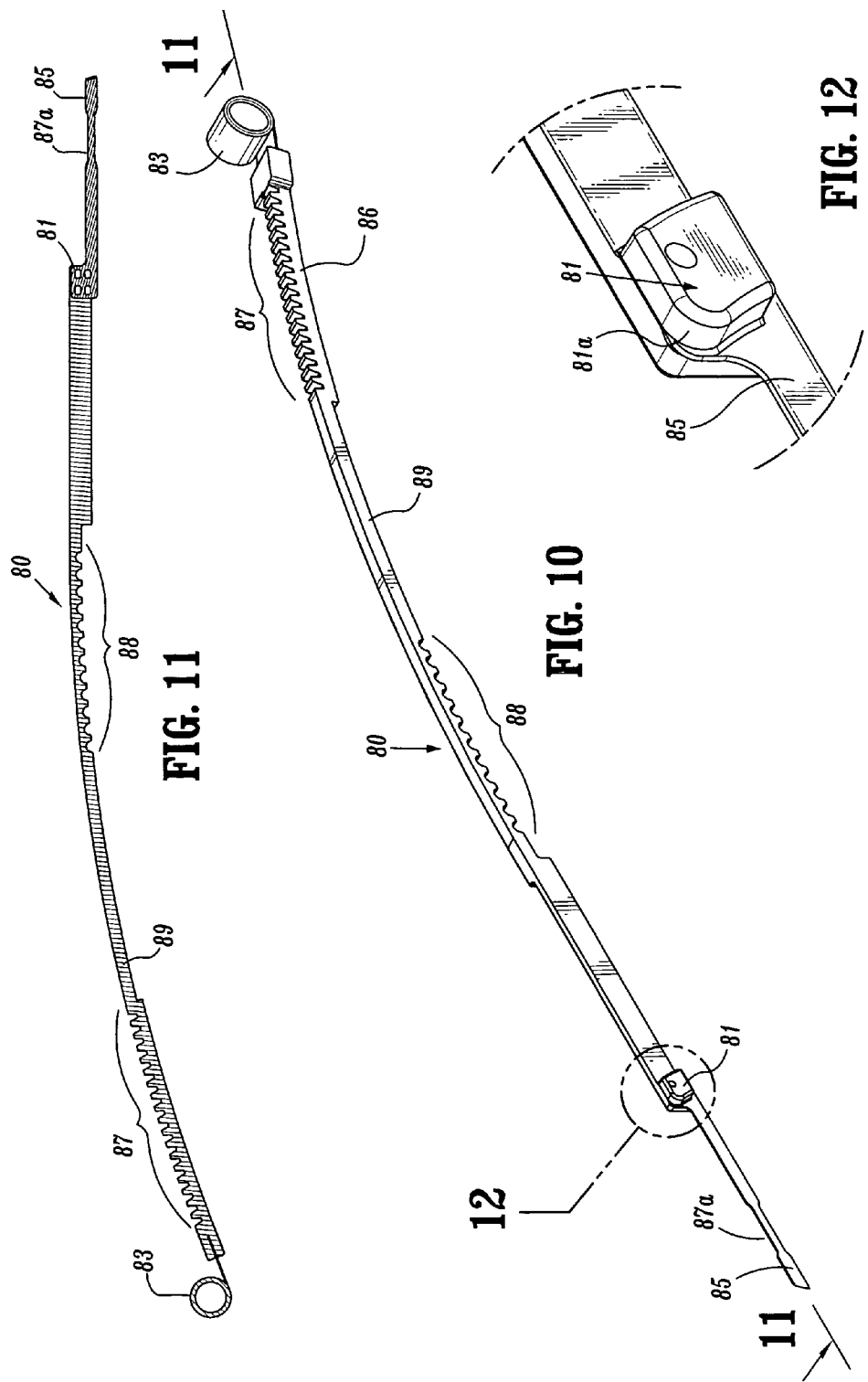

OPEN VESSEL SEALING INSTRUMENT WITH HOURGLASS CUTTING MECHANISM AND OVER-RATCHET SAFETY

CROSS REFERENCE TO RELATED APPLICATION

The present application claims the benefit of priority to U.S. Provisional Application Ser. No. 60/523,387 filed on Nov. 19, 2003 by Moses et al. and is a continuation-in-part to U.S. patent application Ser. No. 10/873,860 filed Jun. 22, 2004 by Moses et al., now U.S. Pat. No. 7,252,667, the entire contents of both of which being incorporated by reference herein.

BACKGROUND

The present disclosure relates to forceps used for open surgical procedures. More particularly, the present disclosure relates to an open forceps which applies a combination of mechanical clamping pressure and electrosurgical energy to seal tissue and a knife which is selectively advanceable to sever tissue along the tissue seal.

TECHNICAL FIELD

A forceps is a plier-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize both mechanical clamping action and electrical energy to effect hemostasis by heating tissue and blood vessels to coagulate and/or cauterize tissue.

Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Vessel sealing or tissue sealing is a recently-developed technology which utilizes a unique combination of radiofrequency energy, pressure and gap control to effectively seal or fuse tissue between two opposing jaw members or the use of heat to destroy tissue (also called "diathermy" or "electrodiathermy"). Vessel sealing is also more than "coagulation" which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

In order to effectively "seal" tissue or vessels, two predominant mechanical parameters must be accurately controlled: 1) the pressure or closure force applied to the vessel or tissue; and 2) the gap distance between the conductive tissue contacting surfaces (electrodes). As can be appreciated, both of these parameters are affected by the thickness of the tissue being sealed. Accurate application of pressure is important for several reasons: to reduce the tissue impedance to a low enough value that allows enough electrosurgical energy through the tissue heating; to overcome the forces of expansion during tissue heating; and to contribute to the end tissue thickness which is an indication of a good seal. It has been determined that a good seal for certain tissues is optimum between about 0.001 and about 0.006 inches.

With respect to smaller vessels or tissue, the pressure applied becomes less relevant and the gap distance between the electrically conductive surfaces becomes more significant for effective sealing. In other words, the chances of the two electrically conductive surfaces touching during activation increases as the tissue thickness and the vessels become smaller.

Commonly owned, U.S. Pat. No. 6,511,480, PCT Patent Application Nos. PCT/US01/11420 and PCT/US01/11218, U.S. patent application Ser. Nos. 10/116,824, 10/284,562 and 10/299,650 all describe various open surgical forceps which seal tissue and vessels. All of these references are hereby incorporated by reference herein. In addition, several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187-190, describes a method for terminating electrosurgical power to the vessel so that charring of the vessel walls can be avoided.

Typically and particularly with respect to open electrosurgical procedures, once a vessel is sealed, the surgeon has to remove the sealing instrument from the operative site, substitute a new instrument and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue sealing line.

Many endoscopic vessel sealing instruments have been designed which incorporate a knife or blade member which effectively severs the tissue after forming a tissue seal. For example, commonly-owned U.S. application Ser. Nos. 10/116,944 and 10/179,863 describe one such endoscopic instrument which effectively seals and cuts tissue along the tissue seal. Other instruments include blade members or shearing members which simply cut tissue in a mechanical and/or electromechanical manner and are relatively ineffective for vessel sealing purposes.

There exists a need to develop an open electrosurgical forceps which is simple, reliable and inexpensive to manufacture and which effectively seals tissue and vessels and which allows a surgeon to utilize the same instrument to effectively sever the tissue along the newly formed tissue seal.

SUMMARY

The present disclosure relates to an open electrosurgical forceps for sealing tissue and includes a pair of first and second shaft members each having a jaw member disposed at a distal end thereof. The jaw members are movable from a first position in spaced relation relative to one another to at least one subsequent position wherein the jaw members cooperate to grasp tissue therebetween. Each jaw member includes an electrically conductive sealing plate for communicating electrosurgical energy through tissue held therebetween upon activation of the forceps. At least one of the jaw members includes a knife channel defined along a length thereof which is dimensioned to reciprocate a cutting mechanism thereal ong.

Preferably, an actuator is included which is operatively connected to one of the shaft members and is configured to selectively advance the cutting mechanism from a first position wherein the cutting mechanism is distally translated through tissue held between the jaw members. The cutting mechanism includes a generally hourglass-shaped flexible knife blade having a notch disposed generally midway therealong which facilitates distal translation of the knife within the knife channel.

In one embodiment, the actuator includes a rack and pinion system having a first gear-like rack connected to the trigger; a second gear-like rack connected to the cutting mechanism; and a pinion disposed between the first and second racks. A safety lockout may also be included which is designed to prevent reciprocation of the cutting mechanism when the jaw members are disposed in the first position. The safety lockout may be dimensioned as part of one of the jaw members and/or part of the cutting mechanism.

Another embodiment according to the present invention includes an open electrosurgical forceps for sealing tissue having a pair of first and second shaft members each including a jaw member disposed at a distal end thereof. The jaw members are movable from a first position in spaced relation relative to one another to at least one subsequent position wherein the jaw members cooperate to grasp tissue therebetween. Preferably, each of the jaw members includes an electrically conductive sealing plate attached thereto for selectively communicating electrosurgical energy through tissue held therebetween to effect a tissue seal. A ratchet is included having first and second ratchet interfaces disposed on the first and second shaft members, respectively. The ratchet is configured to maintain a pressure between jaw members within the range of about 3 kg/cm$^2$ to about 16 kg/cm$^2$. The ratchet preferably includes a stop disposed on one of the shaft members to prevent over pressurizing of the jaw members beyond the first and second ratchet interfaces.

Preferably, the forceps further includes a knife channel defined along a length of at least one of the jaw members. The knife channel is dimensioned to reciprocate a cutting mechanism therealong. An actuator is preferably included which is operatively connected to one of the shaft members and selectively advances the cutting mechanism from a first position wherein the cutting mechanism is disposed proximal to tissue held between the jaw members to at least one subsequent position wherein the cutting mechanism is disposed distal to tissue held between the jaw members.

BRIEF DESCRIPTION OF THE DRAWINGS

Various embodiments of the subject instrument are described herein with reference to the drawings wherein:

FIG. 3 is an internal, perspective view of the forceps of FIG. 1A showing a rack and pinion actuating mechanism for advancing the cutting mechanism and a series of internally disposed electrical connections for energizing the forceps;

FIG. 4 is an internal, side view of the forceps showing the rack and pinion actuating mechanism and the internally disposed electrical connections;

FIG. 10 is an enlarged, perspective view of the cutting mechanism;

FIG. 11 is a side cross section along lines 11-11 of FIG. 10;

FIG. 12 is an enlarged, perspective view of the area of detail in FIG. 10;

DETAILED DESCRIPTION

Figure 1A:
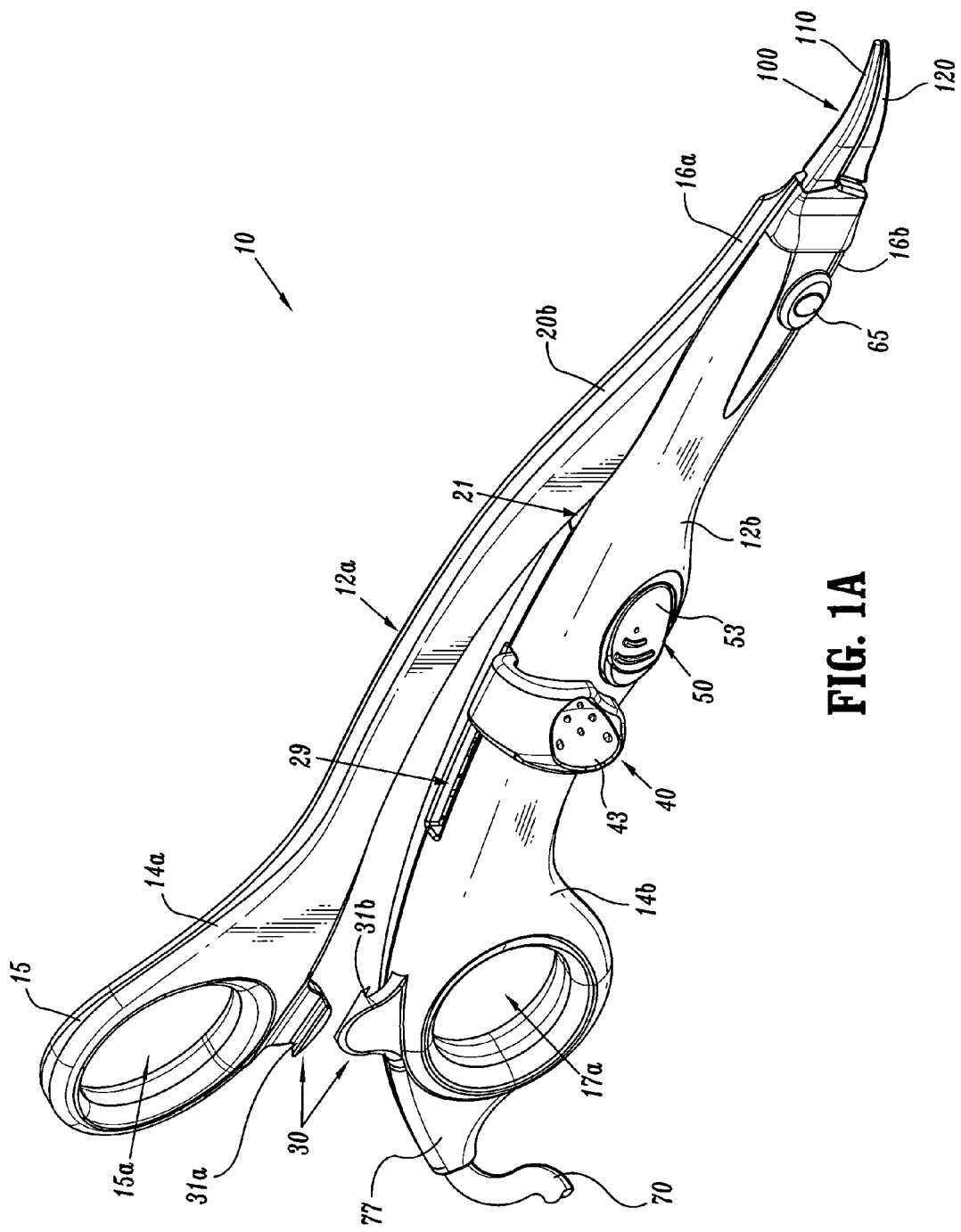
FIG. 1A is a left, front perspective view of an open forceps with a cutting mechanism according to the present disclosure.

Referring now to FIGS. 1-7A, a forceps 10 for use with open surgical procedures includes elongated shaft portions 12a and 12b each having a proximal end 14a, 14b and a distal end 16a and 16b, respectively. In the drawings and in the descriptions which follow, the term "proximal", as is traditional, will refer to the end of the forceps 10 which is closer to the user, while the term "distal" will refer to the end which is further from the user.

The forceps 10 includes an end effector assembly 100 which attaches to the distal ends 16a and 16b of shafts 12a and 12b, respectively. As explained in more detail below, the end effector assembly 100 includes pair of opposing jaw members 110 and 120 which are pivotably connected about a pivot pin 65 and which are movable relative to one another to grasp tissue.

Preferably, each shaft 12a and 12b includes a handle 15 and 17, respectively, disposed at the proximal end 14a and 14b thereof which each define a finger hole 15a and 17a, respectively, therethrough for receiving a finger of the user. As can be appreciated, finger holes 15a and 17a facilitate movement of the shafts 12a and 12b relative to one another which, in turn, pivot the jaw members 110 and 120 from an open position wherein the jaw members 110 and 120 are disposed in spaced relation relative to one another to a clamping or closed position wherein the jaw members 110 and 120 cooperate to grasp tissue therebetween.

Figure 7A:
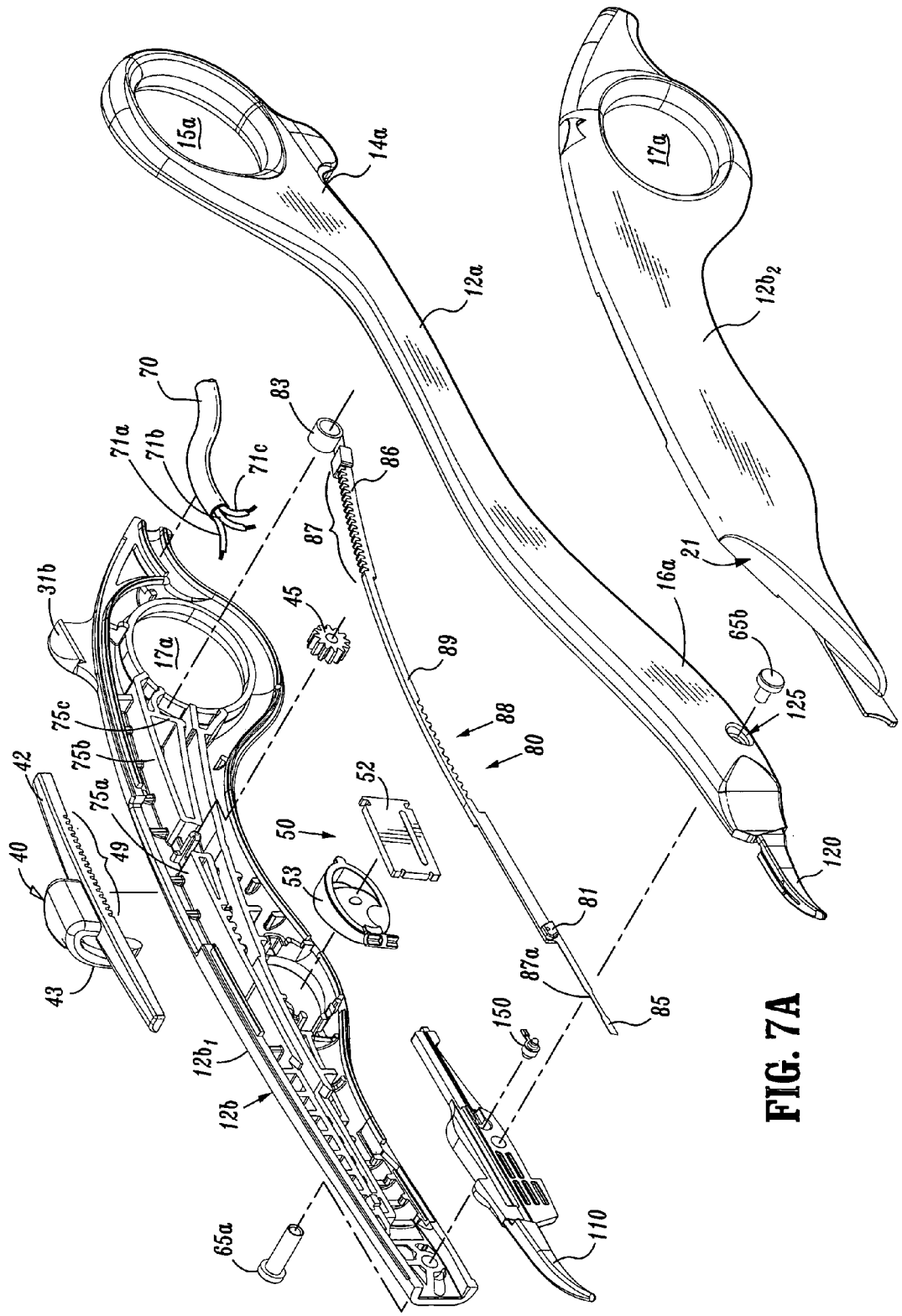
FIG. 7A is a perspective view of the forceps of FIG. 1A with parts separated.
Figure 7B:
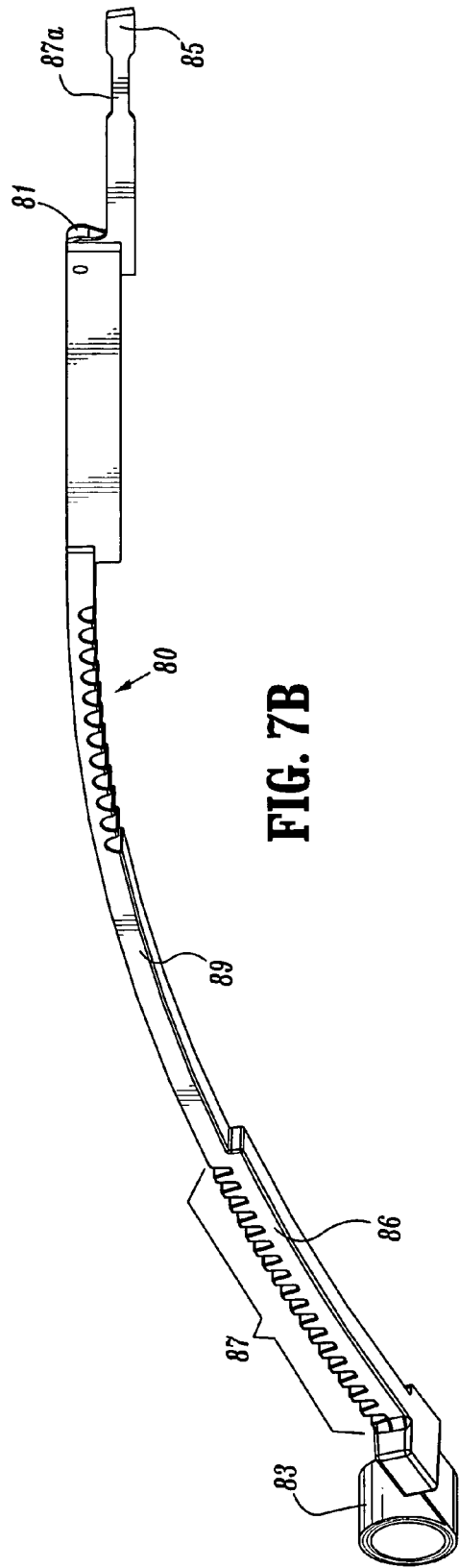
FIG. 7B is an enlarged perspective view of a cutting mechanism of FIG. 7A.
Figure 7C:
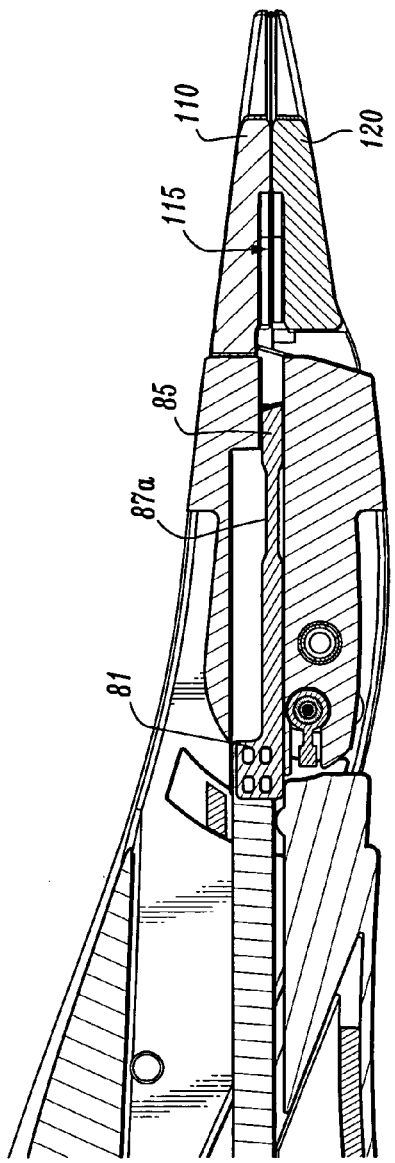
FIG. 7C is an enlarged cross sectional view of an end effector assembly of the forceps of FIG. 1C.
Figure 8:
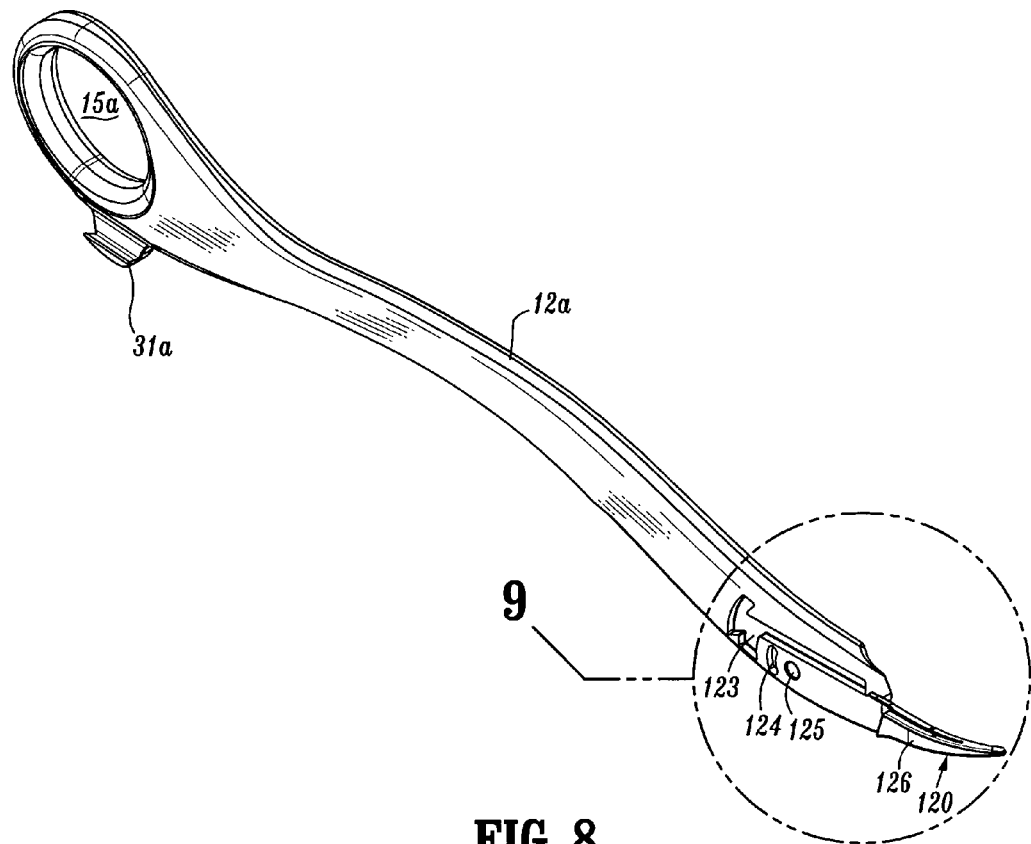
FIG. 8 is a perspective view of one shaft of the forceps of FIG. 1A.

As best seen in FIG. 7A-7C, shaft 12b is constructed from two components, namely, 12b1 and 12b2, which matingly engage one another about the distal end 16a of shaft 12a to form shaft 12b. It is envisioned that the two component halves 12b1 and 12b2 may be ultrasonically-welded together at a plurality of different weld points or the component halves 12b1 and 12b2 may be mechanically engaged in any other known fashion, snap-fit, glued, screwed, etc. After component halves 12b1 and 12b2 are welded together to form shaft 12b, shaft 12a is secured about pivot 65 and positioned within a cut-out or relief 21 defined within shaft portion 12b2 such that shaft 12a is movable relative to shaft 12b. More particularly, when the user moves the shaft 12a relative to shaft 12b to close or open the jaw members 110 and 120, the distal portion of shaft 12a moves within cutout 21 formed within portion 12b2. It is envisioned that configuring the two shafts 12a and 12b in the fashion facilitates gripping and reduces the overall size of the forceps 10 which is especially advantageous during surgeries in small cavities.

Figure 1B:
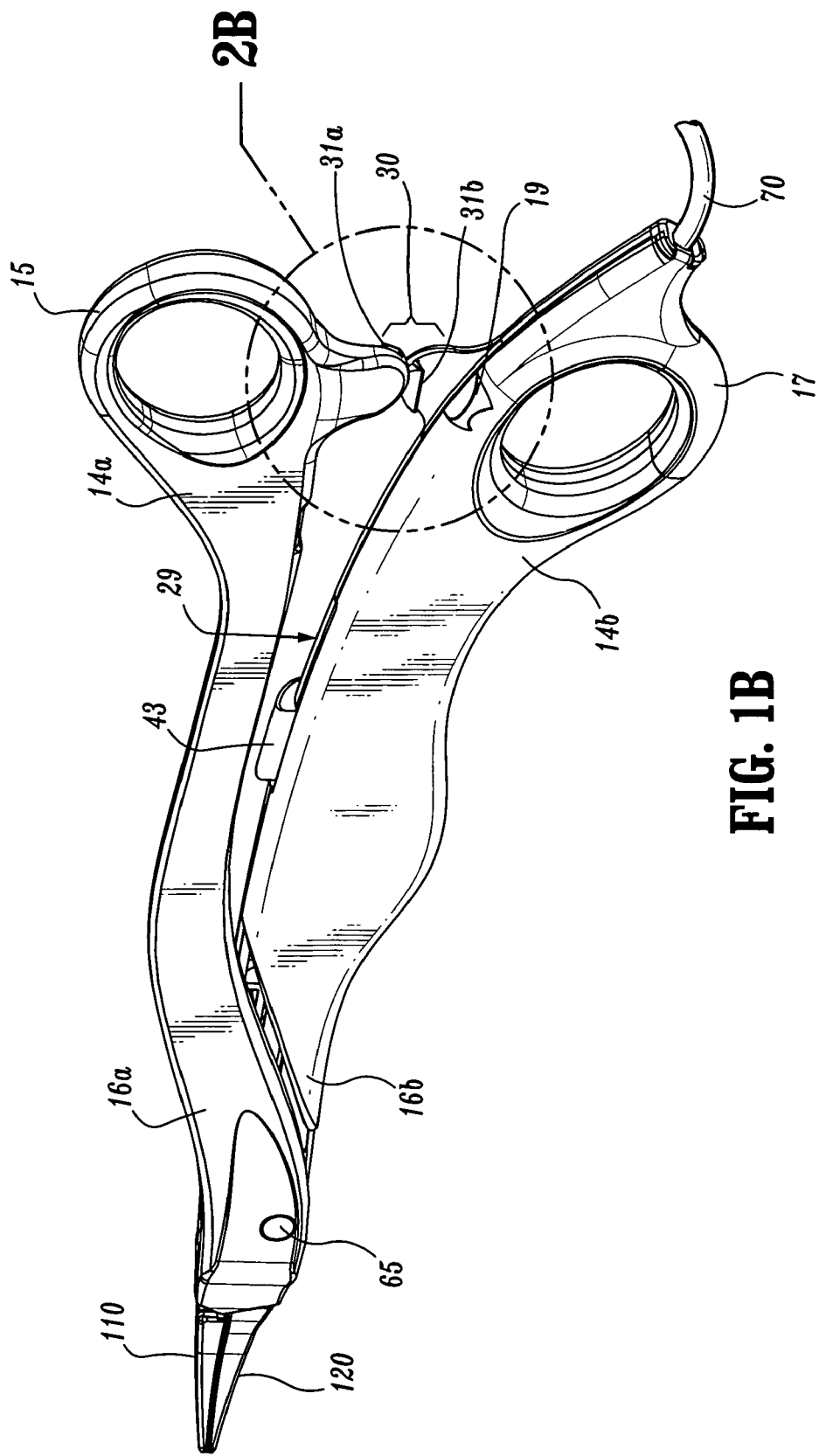
FIG. 1B is a right, rear perspective view of the forceps of FIG. 1A shown in open configuration.
Figure 1C:
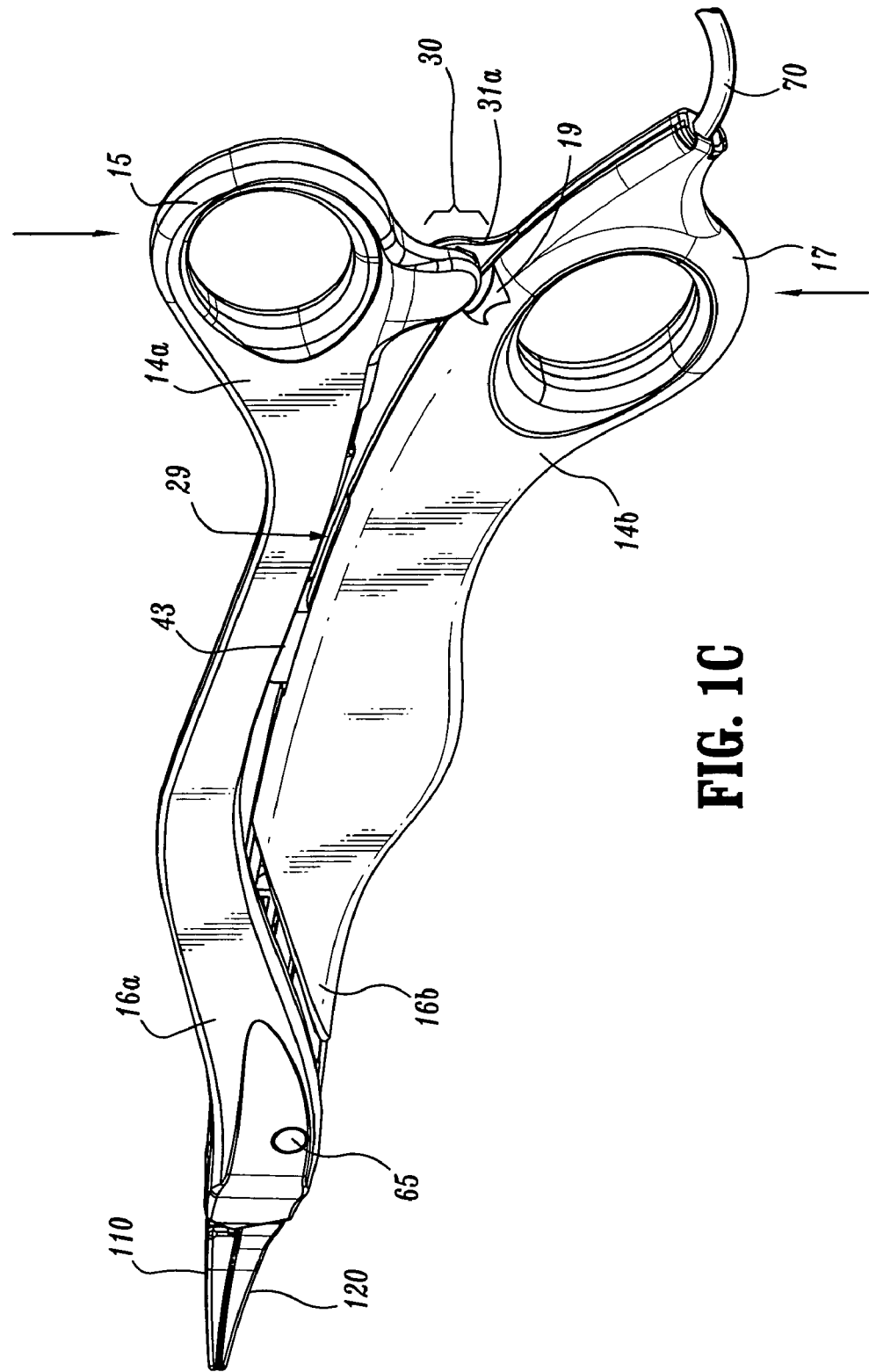
FIG. 1C is a right, rear perspective view of the forceps of FIG. 1A shown in closed configuration.

As best illustrated in FIG. 1A-1C, one of the shafts, e.g., 12b, includes a proximal shaft connector 77 which is designed to connect the forceps 10 to a source of electrosurgical energy such as an electrosurgical generator (not shown). The proximal shaft connector 77 electromechanically engages an electrosurgical cable 70 such that the user may selectively apply electrosurgical energy as needed. Alternatively, the cable 70 may be feed directly into shaft 12b (or 12a).

As explained in more detail below, the distal end of the cable 70 connects to a handswitch 50 to permit the user to selectively apply electrosurgical energy as needed to seal tissue grasped between jaw members 110 and 120. More particularly, the interior of cable 70 houses leads 71a, 71b and 71c which upon activation of the handswitch 50 conduct the different electrical potentials from the electrosurgical generator to the jaw members 110 and 120 (See FIGS. 3 and 4). As can be appreciated, positioning the switch 50 on the forceps 10 gives the user more visual and tactile control over the application of electrosurgical energy. These aspects are explained below with respect to the discussion of the handswitch 50 and the electrical connections associated therewith.

The two opposing jaw members 110 and 120 of the end effector assembly 100 are pivotable about pin 65 from the open position to the closed position for grasping tissue therebetween. Preferably, pivot pin 65 consists of two component halves 65a and 65b which matingly engage and pivotably secure the shafts 12a and 12b during assembly such that the jaw members 110 and 120 are freely pivotable between the open and closed positions. For example, the pivot pin 65 may be configured to be spring loaded such that the pivot snap fits together at assembly to secure the two shafts 12a and 12b for rotation about the pivot pin 65.

The tissue grasping portions of the jaw members 110 and 120 are generally symmetrical and include similar component features which cooperate to permit facile rotation about pivot pin 65 to effect the grasping and sealing of tissue. As a result and unless otherwise noted, jaw member 110 and the operative features associated therewith are initially described herein in detail and the similar component features with respect to jaw member 120 will be briefly summarized thereafter. Moreover, many of the features of the jaw members 110 and 120 are described in detail in commonly-owned U.S. patent application Ser. Nos. 10/284,562, 10/116,824, 09/425, 696, 09/178,027 and PCT Application Serial No. PCT/US01/11420 the contents of which are all hereby incorporated by reference in their entirety herein.

Figure 14:
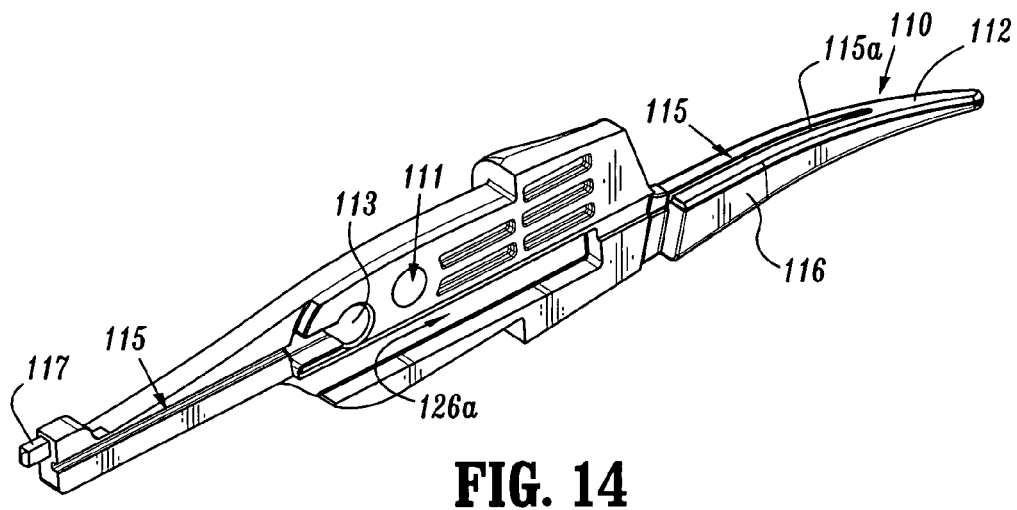
FIG. 14 is an enlarged, left perspective view of the one of the jaw members of the forceps of FIG. 1A.
Figure 15:
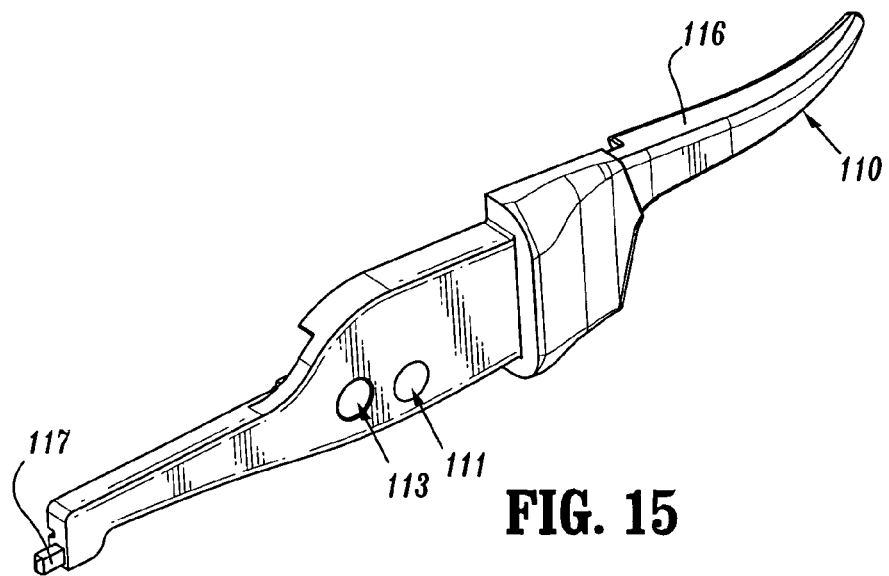
FIG. 15 is an enlarged, right perspective view of the jaw member of FIG. 14.
Figure 16:
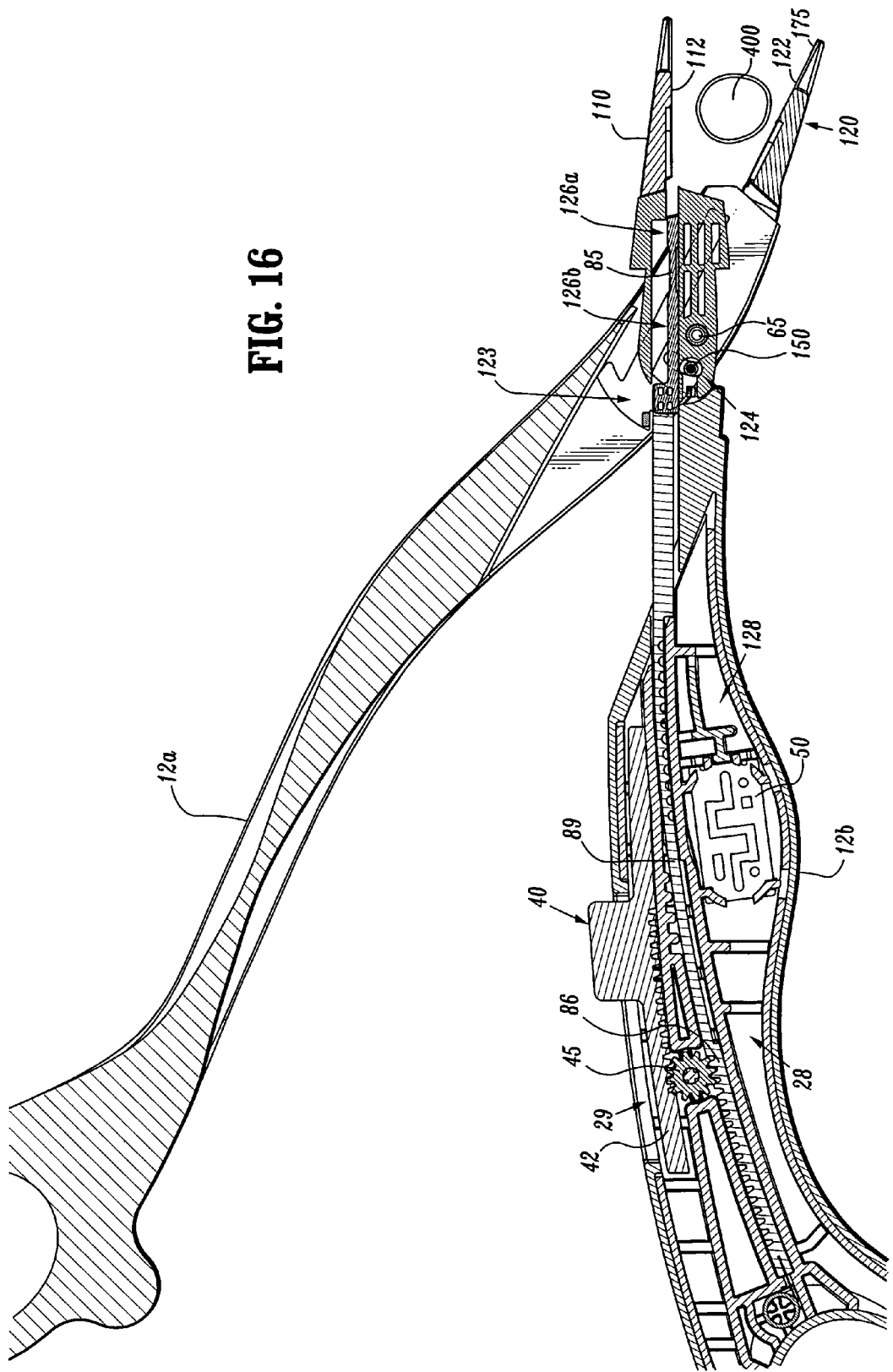
FIG. 16 is side cross sectional view showing the forceps in open configuration for grasping tissue.

As best shown in FIGS. 14 and 15, jaw member 110 includes an insulated outer housing 116 which is dimensioned to mechanically engage an electrically conductive sealing surface 112. The outer insulative housing 116 extends along the entire length of jaw member 110 to reduce alternate or stray current paths during sealing and/or incidental burning of tissue. The electrically conductive surface 112 conducts electrosurgical energy of a first potential to the tissue upon activation of the handswitch 50. Insulated outer housing 116 is dimensioned to securely engage the electrically conductive sealing surface 112. It is envisioned that this may be accomplished by stamping, by overmolding, by overmolding a stamped electrically conductive sealing plate and/or by overmolding a metal injection molded seal plate. Other methods of affixing the seal surface 112 to the outer housing 116 are described in detail in one or more of the above-identified references. Preferably, the jaw members 110 and 120 are made from a conductive material and powder coated with an insulative coating to reduce stray current concentrations during sealing.

It is also contemplated that the electrically conductive sealing surface 112 may include an outer peripheral edge which has a radius and the insulated outer housing 116 meets the electrically conductive sealing surface 112 along an adjoining edge which is generally tangential to the radius and/or meets along the radius. Preferably, at the interface, the electrically conductive surface 112 is raised relative to the insulated outer housing 116. Alternatively, the jaw member 110 including the sealing plate 112 and the outer insulative housing 116 may be formed as part of a molding process to facilitate manufacturing and assembly. These and other envisioned embodiments are discussed in commonly-owned, co-pending PCT Application Serial No. PCT/US01/11412 and commonly owned, co-pending PCT Application Serial No. PCT/US01/11411, the contents of both of these applications being incorporated by reference herein in their entirety.

Preferably, the insulated outer housing 116 and the electrically conductive sealing surface 112 are dimensioned to limit and/or reduce many of the known undesirable effects related to tissue sealing, e.g., flashover, thermal spread and stray current dissipation. All of the aforementioned and cross referenced manufacturing techniques produce an electrode having an electrically conductive surface 112 which is substantially surrounded by an insulated outer housing 116.

Likewise, jaw member 120 includes similar elements which include: an outer housing 126 which engages an electrically conductive sealing surface 122 and an electrically conducive sealing surface 122 which conducts electrosurgical energy of a second potential to the tissue upon activation of the handswitch 50.

Figure 18:
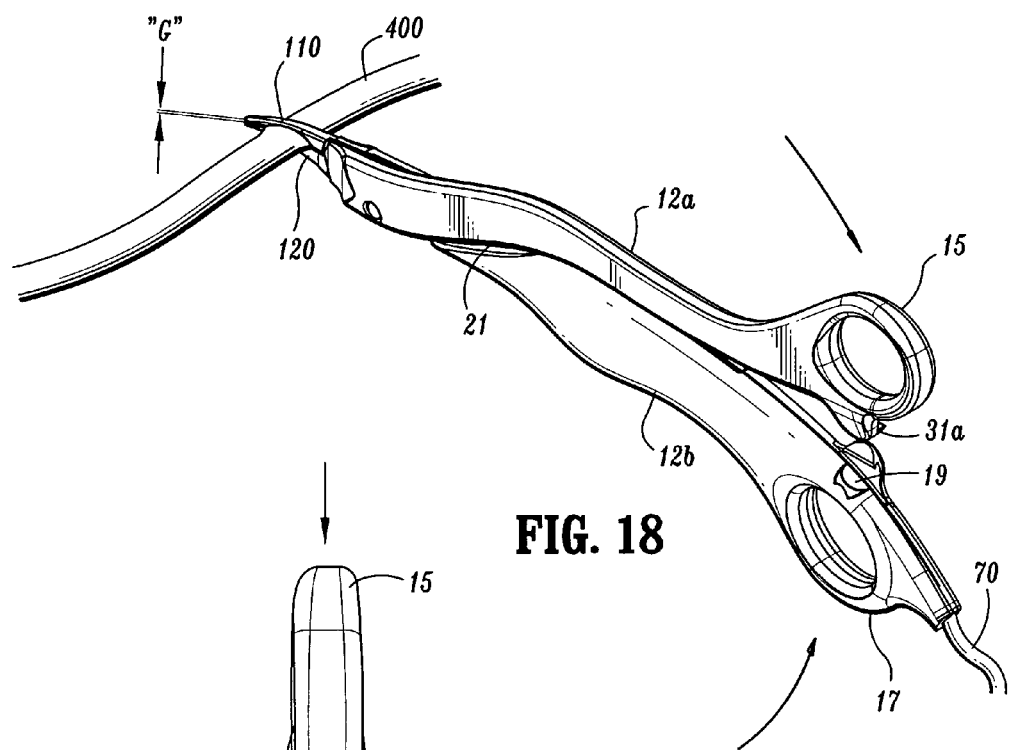
FIG. 18 is a rear, perspective view of the forceps of FIG. 1A shown grasping tissue with a ratchet mechanism shown prior to engagement.
Figure 19:
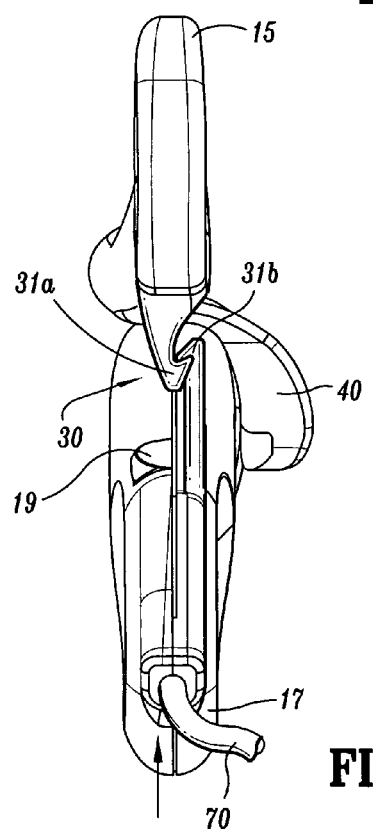
FIG. 19 is a rear view of the forceps of FIG. 1A showing the ratchet mechanism engaged.
Figure 20:
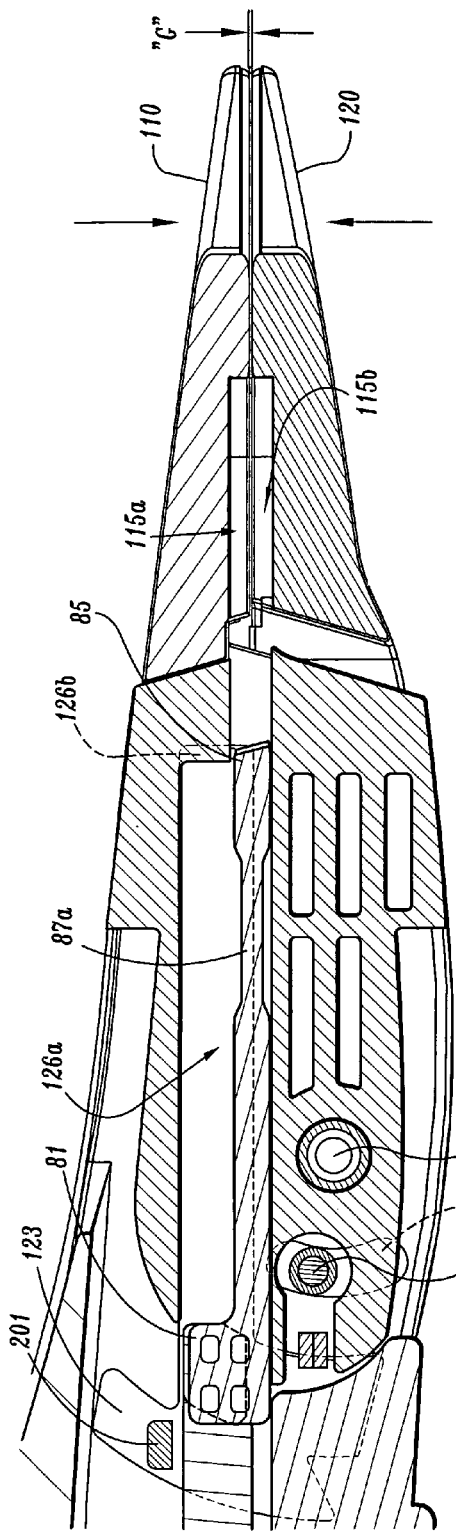
FIG. 20 is a greatly-enlarged, side cross sectional view showing the forceps in a closed position and defining a gap distance "G" between opposing jaw members.

It is envisioned that one of the jaw members, e.g., 120, includes at least one stop member 175 disposed on the inner facing surface of the electrically conductive sealing surface 122 (and/or 112). Alternatively or in addition, the stop member 175 may be positioned adjacent to the electrically conductive sealing surfaces 112, 122 or proximate the pivot pin 65. The stop member(s) is preferably designed to facilitate gripping and manipulation of tissue and to define a gap "G" between opposing jaw members 110 and 120 during sealing (See FIGS. 18 and 20). Preferably the separation distance during sealing or the gap distance "G" is within the range of about 0.001 inches (~0.03 millimeters) to about 0.006 inches (~0.016 millimeters). In one particular preferred embodiment and as best shown on FIG. 9 a stop member 175 is positioned on either side of the knife channel 115 generally midway along the length of the bottom jaw member 120. In addition or alternatively, another stop member may be positioned at the distal end of the jaw member 120 to control the distance between the sealing surface 112 and 122 when the jaw members close about tissue to effect consistent and effective vessel sealing (See FIG. 24B).

A detailed discussion of these and other envisioned stop members 175 as well as various manufacturing and assembling processes for attaching, disposing, depositing and/or affixing the stop members to the electrically conductive sealing surfaces 112, 122 are described in commonly-assigned, co-pending PCT Application Serial No. PCT/US01/11222 which is hereby incorporated by reference in its entirety herein.

As mentioned above, two mechanical factors play an important role in determining the resulting thickness of the sealed tissue and effectiveness of the seal, i.e., the pressure applied between opposing jaw members 110 and 120 and the gap "G" between the opposing jaw members 110 and 120 (or opposing seal surfaces 112 and 122 during activation). It is known that the thickness of the resulting tissue seal cannot be adequately controlled by force alone. In other words, too much force and the sealing surfaces 112 and 122 of the two jaw members 110 and 120 would touch and possibly short resulting in little energy traveling through the tissue thus resulting in a bad seal. Too little force and the seal would be too thick. Applying the correct force is also important for other reasons: to oppose the walls of the vessel; to reduce the tissue impedance to a low enough value that allows enough current through the tissue; and to overcome the forces of expansion during tissue heating in addition to contributing towards creating the required end tissue thickness which is an indication of a good seal.

Preferably, the seal surfaces 112 and 122 are relatively flat to avoid current concentrations at sharp edges and to avoid arcing between high points. In addition and due to the reaction force of the tissue when engaged, jaw members 110 and 120 are preferably manufactured to resist bending, i.e., tapered along their length which provides a constant pressure for a constant tissue thickness at parallel and the thicker proximal portion of the jaw members 110 and 120 will resist bending due to the reaction force of the tissue.

Figure 9:
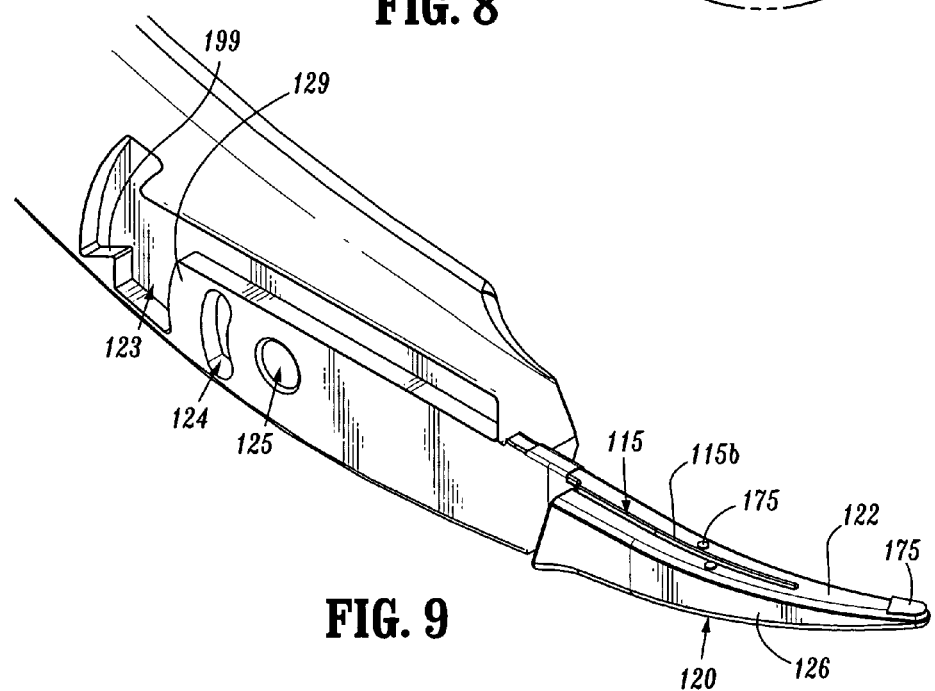
FIG. 9 is an enlarged, perspective view showing the area of detail in FIG. 8.
Figure 13:
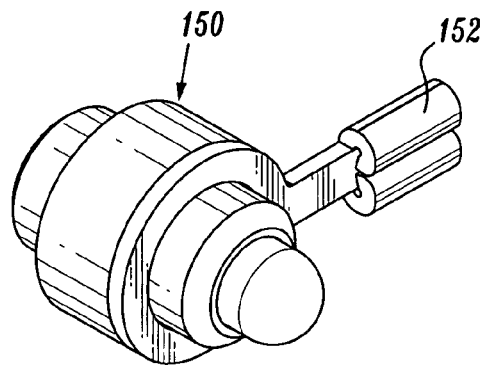
FIG. 13 is a greatly-enlarged perspective view of a distal electrical connector of the forceps of FIG. 1A.

As best seen in FIGS. 9 and 14, the jaw members 110 and 120 include a knife channel 115 disposed therebetween which is configured to allow reciprocation of a cutting mechanism 80 therewithin. One example of a knife channel is disclosed in commonly-owned U.S. patent application Ser. No. 10/284,562 the entire contents of which are hereby incorporated by reference herein. Preferably, the complete knife channel 115 is formed when two opposing channel halves 115a and 115b associated with respective jaw members 110 and 120 come together upon grasping of the tissue. It is envisioned that the knife channel 115 may be tapered or some other configuration which facilitates or enhances cutting of the tissue during reciprocation of the cutting mechanism 80 in the distal direction. Moreover, the knife channel 115 may be formed with one or more safety features which prevent the cutting mechanism 80 from advancing through the tissue until the jaw members 110 and 120 are closed about the tissue.

The arrangement of shaft 12b is slightly different from shaft 12a. More particularly, shaft 12b is generally hollow to define a chamber 28 therethrough which is dimensioned to house the handswitch 50 (and the electrical components associated therewith), the actuating mechanism 40 and the cutting mechanism 80. As best seen in FIGS. 3, 4 and 7A, the actuating mechanism 40 includes a rack and pinion system having first and second gear tracks 42 and 86, respectively, and a pinion 45 to advance the cutting mechanism 80. More particularly, the actuating mechanism 40 includes a trigger or finger tab 43 which is operatively associated with a first gear rack 42 such that movement of the trigger or finger tab 43 moves the first rack 42 in a corresponding direction. The actuating mechanism 40 mechanically cooperates with a second gear rack 86 which is operatively associated with a drive rod 89 and which advances the entire cutting mechanism 80 as will be explained in more detail below. Drive rod 89 includes a distal end 81 which is configured to mechanically support the cutting blade 87 and which acts as part of a safety lockout mechanism as explained in more detail below.

Figure 23:
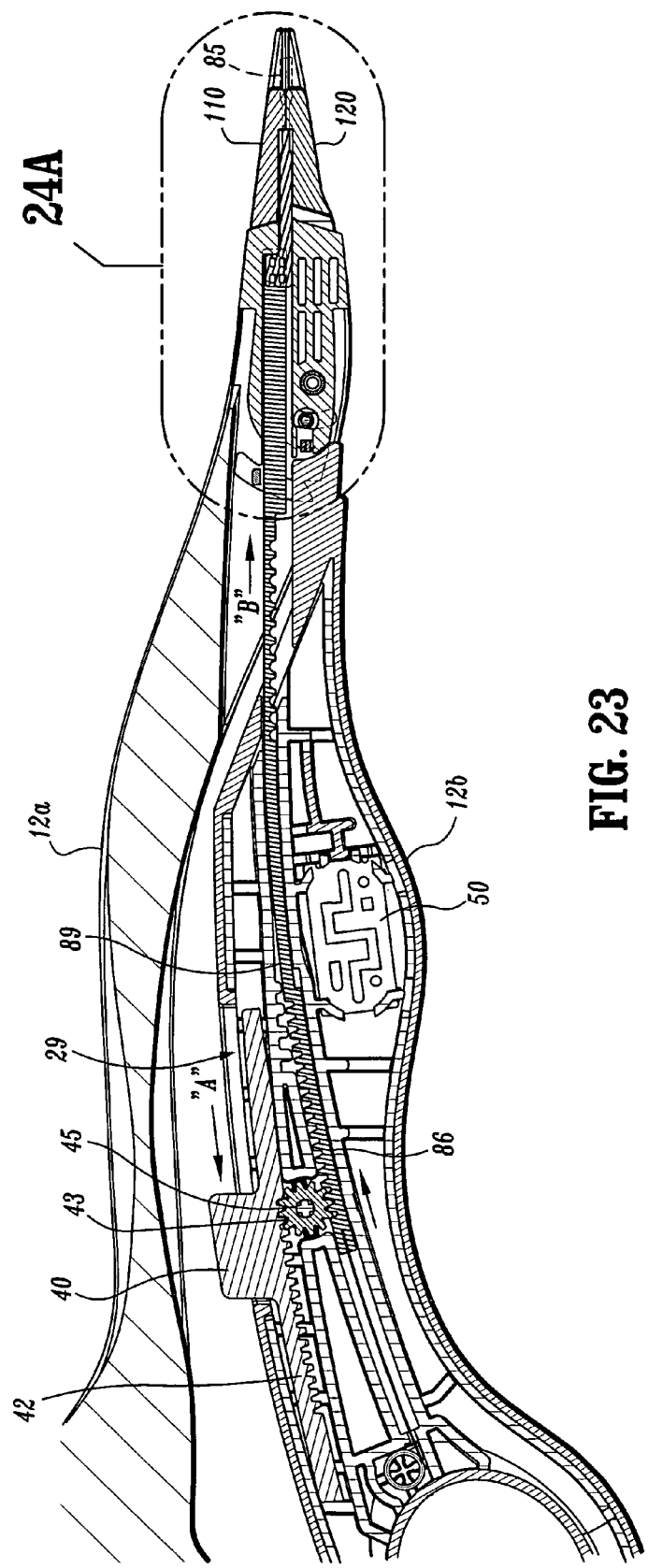
FIG. 23 is a side cross sectional view showing the forceps in a closed position and showing the activation and advancement of the cutting mechanism.

Interdisposed between the first and second gear racks 42 and 86, respectively, is a pinion gear 45 which mechanically meshes with both gear racks 42 and 86 and converts proximal motion of the trigger 43 into distal translation of the drive rod 89 and vice versa. More particularly, when the user pulls the trigger 43 in a proximal direction within a predisposed channel 29 in the shaft 12b (See arrow "A" in FIG. 23), the first rack 42 is translated proximally which, in turn, rotates the pinion gear 45 in a counter-clockwise direction. Rotation of the pinion gear 45 in a counter-clockwise direction forces the second rack 86 to translate the drive rod 89 distally (See arrow "B" in FIG. 23) which advances the blade 87 of the cutting mechanism 80 through tissue 400 grasped between jaw members 110 and 120, i.e., the cutting mechanism 80, e.g., knife, blade, wire, etc., is advanced through channel 115 upon distal translation of the drive rod 89.

It is envisioned that multiple gears or gears with different gear ratios may be employed to reduce surgical fatigue which may be associated with advancing the cutting mechanism 80. In addition, it is contemplated the gear tracks 42 and 86 are configured to include a plurality of gear teeth tracks 43 and 87, respectively, which may be of different length to provide additional mechanical advantage for advancing the jaw members 110 and 120 through tissue. The rack and pinion arrangement may be curved for spatial purposes and to facilitate handling and/or to enhance the overall ergonomics of the forceps 10.

A spring 83 may be employed within chamber 28 to bias the first rack 42 upon proximal movement thereof such that upon release of the trigger 43, the force of the spring 83 automatically returns the first rack 42 to its distal most position within channel 29. Obviously, spring 83 may be operatively connected to bias the second rack 86 to achieve the same purpose.

Preferably, the trigger 43 includes one or more ergonomically friendly features which enhance the tactile feel and grip for the user to facilitate actuation of the finger tab 43. Such features may include, raised protuberances, rubber inserts, scallops and gripping surfaces and the like. In addition, the downward orientation of the trigger 43 is believed to be particularly advantageous since this orientation tends to minimize accidental or inadvertent activation of the trigger 43 during handling. Moreover, it is contemplated that integrally associating (molding or otherwise forming) the trigger 43 and the gear rack 42 during the manufacturing process minimizes the number of parts which, in turn, simplifies the overall assembly process.

As best seen in FIGS. 5, 9, 10, 11, 12, 17, 20 and 23, a safety lockout mechanism 200 is associated with the actuating assembly 40 and the cutting mechanism 80 to prevent advancement of the cutting mechanism 80 until the jaw members 110 and 120 are positioned and closed about tissue. Other lockout mechanisms and features are described in commonly-owned U.S. application Ser. Nos. 10/460,926, 10/461,550, 10/462,121 and U.S. Provisional Application Ser. No. 60/523,387 which are all incorporated by reference herein in their entirety. The safety lockout mechanism includes a series of inter-cooperating elements which work together to prevent unintentional firing of the cutting mechanism 80 when the jaw members 110 and 120 are disposed in the open position.

More particularly, the distal end 81 of the cutting mechanism 80 is dimensioned to reciprocate within a channel 126b defined in the proximal end of jaw member 120 when jaw member 110 and 120 are disposed in a closed position (see FIG. 9). The proximal end of channel 126b defines a recess or relieved portion 123 therein which includes a forward stop 129 which abuts and prevents advancement of the distal end 81 of the cutting mechanism 80 when the jaw members 110 and 120 are disposed in the open position (See FIGS. 9 and 17). The proximal portion of jaw member 120 also includes a guide slot 124 defined therethrough which allows a terminal connector 150 or so called "POGO" pin to ride therein upon movement of the jaw members 110 and 120 from the open to closed positions (See FIG. 17 and 24A). In addition, the proximal end includes an aperture 125 defined therethrough which houses the pivot pin 65. Jaw member 110 also includes a channel 126a which aligns with channel 126b when the jaw members 110 and 120 are disposed in the closed position about tissue.

Figure 17:
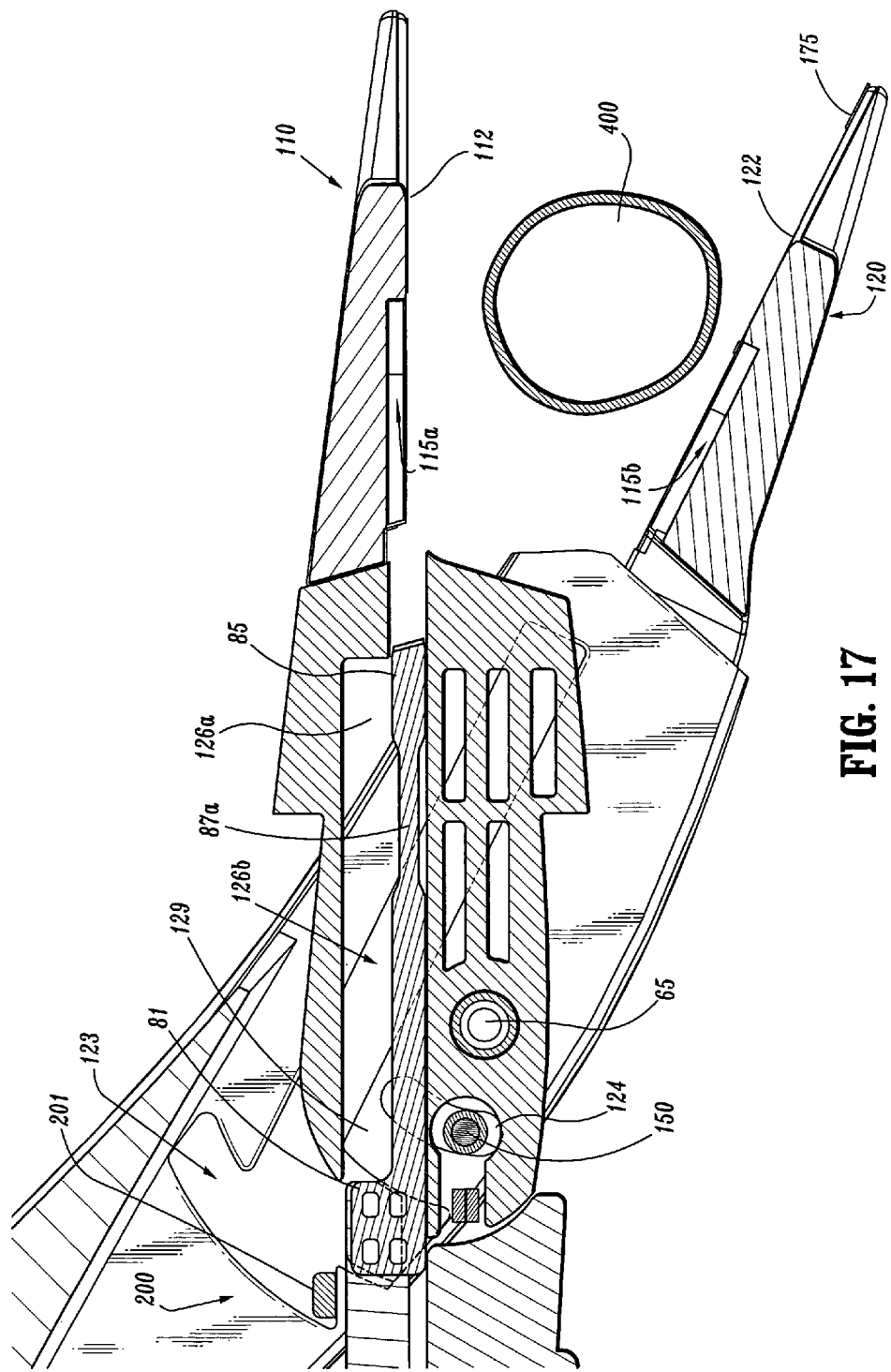
FIG. 17 is a side cross sectional view showing the area of detail in FIG. 16.
Figure 24A:
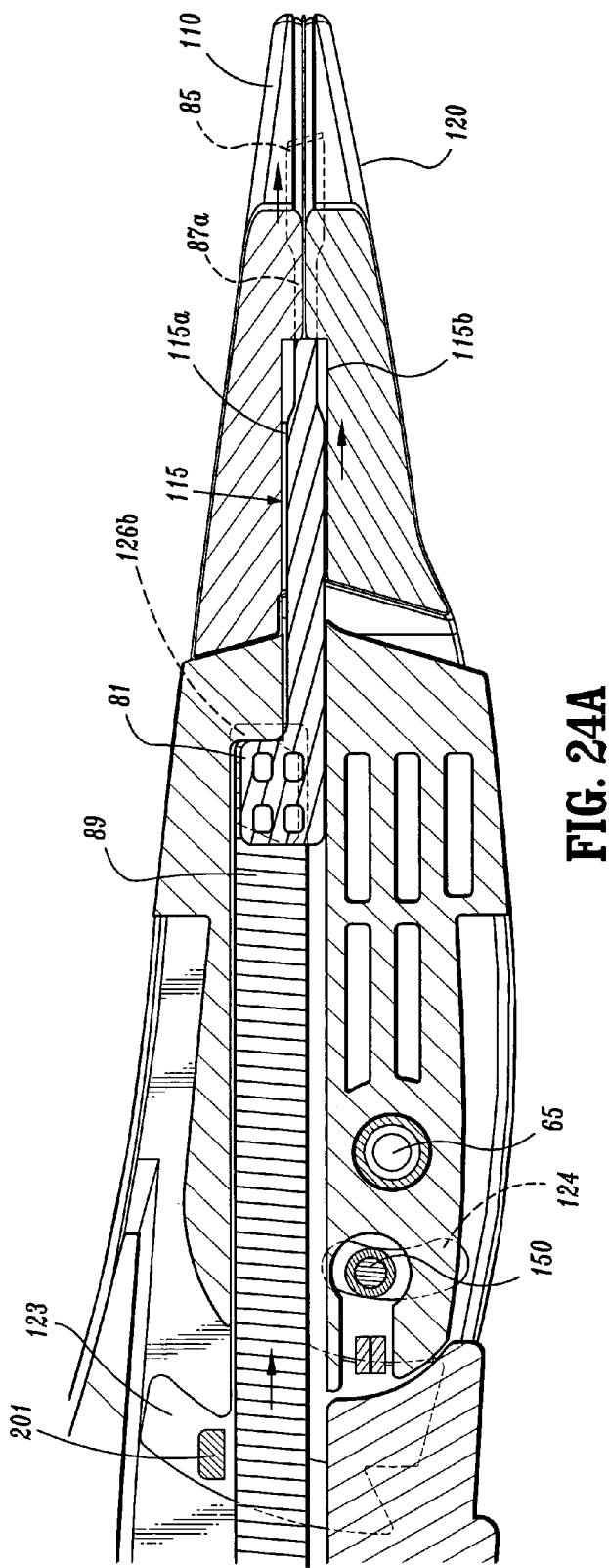
FIG. 24A is an enlarged view of the area of detail in FIG. 23.

As best shown in FIGS. 17 and 24A which show the jaw members 110 and 120 in open and closed orientations, respectively, the operation of the lockout mechanism 200 is easily described. When jaw member 120 is rotated with respect to jaw member 110 about pivot 65 a flanged portion 81a of the distal end 81 of cutting mechanism 80 is slidingly incorporated within recess 123 and against stop 129 located in the proximal end of jaw member 120 (See FIG. 12). The stop 129 prevents the cutting mechanism 80 from moving forward due to unintentional actuation of the trigger 43. At the same time, the terminal connector 150 moves freely within slot 124 upon rotation of the jaw members 110 and 120. It is envisioned that the terminal connector 150 is seated within aperture 151 within jaw member 110 and rides within slot 124 of jaw member 120 to provide a "running" or "brush" contact to supply electrosurgical energy to jaw member 120 during the pivoting motion of the forceps 10 (See FIG. 17). Recess 123 also includes a rim or flange 199 which prevents over-rotation of shaft 12a relative to shaft 12b. More particularly and as best seen on FIGS. 9 and 17, flange 199 is dimensioned to abut a stop 201 disposed within forceps 110 when rotated to a fully open position to prevent unintentional over-rotation of the forceps 10.

When the jaw members 110 and 120 are moved to the closed position as illustrated in FIG. 24A, the safety lockout mechanism 200 automatically disengages to allow distal advancement of the cutting mechanism 80. More particularly, when the jaw members 110 and 120 are closed about tissue, the distal end 81 including the flanged portion 81a automatically aligns within the channels 126a and 126 of jaw members 110 and 120, respectively, to allow selective actuation of the cutting mechanism 80. As shown in FIG. 24A, the distal end 81 advances through channel 126a and 126b forcing the knife blade 87 through knife channel 115 (115a and 115b) to cut tissue. As described above, when the actuating flange 43 is released, spring 83 biases the drive rod 89 back to the proximal-most position (not shown) which, in turn, re-aligns distal end 81 with recess 123 to allow the jaw members 110 and 120 to be moved to the open position to release the tissue 400.

It is envisioned that the safety lockout mechanism 200 may include one or more electrical or electromechanical sensors (not shown) which prevent the cutting mechanism 80 from advancing through tissue until a tissue seal has been created. For example, the safety lockout mechanism 200 could include a sensor which upon completion of a tissue seal activates a switch or release (not shown) which unlocks the cutting mechanism 80 for advancement through tissue.

Figure 24B:
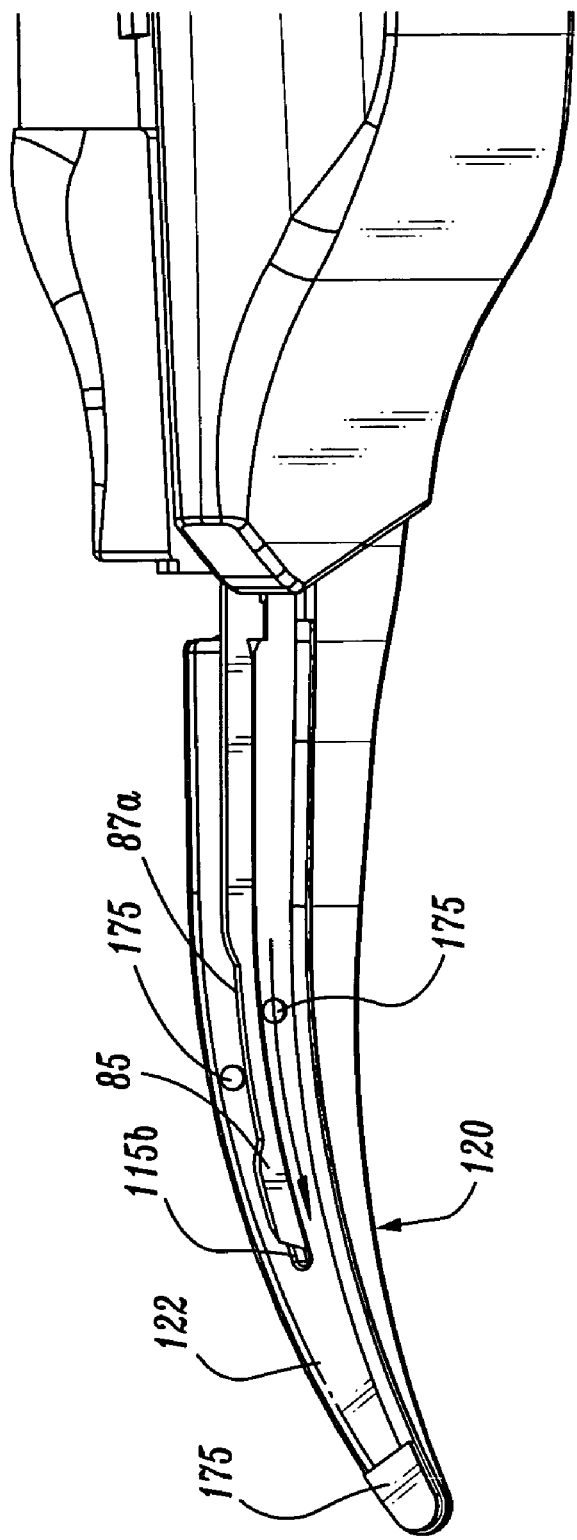
FIG. 24B is an enlarged perspective view of the bottom jaw member showing the cutting mechanism in a distally advanced orientation.

As best seen in FIGS. 9, 10 and 24B, blade 87 is flexible so it easily advances through the curved knife channel 115. For example, upon distal advancement of the cutting mechanism 80, the cutting blade 87 will simply flex and ride around the knife channel 115 through the tissue 400 held between jaw members 110 and 120. In one particular embodiment and as shown, the blade 87 is flexible and is generally hourglass in configuration and includes a notched area 87a disposed about midway along the blade 87. The notch 87a reduces the side profile of the blade to facilitate the cutting process. More particularly, the hourglass design of the blade allows the blade 87 to move more easily along the curved knife channel 115 during distal translation thereof. A curved blade (not shown) may also be utilized which has a similar radius of curvature as the knife channel 115 such that the blade will travel through the knife channel 115 without contacting the surfaces of the knife channel 115.

FIGS. 1A, 2A-2C and 19 show a ratchet 30 for selectively locking the jaw members 110 and 120 relative to one another in at least one position during pivoting. A first ratchet interface 31a extends from the proximal end 14a of shaft member 12a towards a second ratchet interface 31b on the proximal end 14b of shaft 12b in general vertical registration therewith such that the inner facing surfaces of each ratchet 31a and 31b abut one another upon closure of the jaw members 110 and 120 about the tissue 400. It is envisioned that each ratchet interface 31a and 31b may include a plurality of step-like flanges (not shown) which project from the inner facing surface of each ratchet interface 31a and 31b such that the ratchet interfaces 31a and 31b interlock in at least one position. Preferably, each position associated with the cooperating ratchet interfaces 31a and 31b holds a specific, i.e., constant, strain energy in the shaft members 12a and 12b which, in turn, transmits a specific closing force to the jaw members 110 and 120.

It is envisioned that the ratchet 30 may include graduations or other visual markings which enable the user to easily and quickly ascertain and control the amount of closure force desired between the jaw members. It is envisioned that the shafts 12a and 12b may be manufactured from a particular plastic material which is tuned to apply a particular closure pressure within the above-specified working range to the jaw members 110 and 120 when ratcheted. As can be appreciated, this simplified the manufacturing process and eliminates under pressurizing and over pressurizing the jaw members 110 and 120 during the sealing process.

The proximal connector 77 may include a stop or protrusion 19 (See FIGS. 1B, 1C, 2B, 2C and 7A) which prevents the user from over pressurizing the jaw members 110 and 120 by squeezing the handle 15 and 17 beyond the ratchet positions. As can be appreciated this facilitates consistent and effective sealing due to the fact that when ratcheted, the forceps 10 are automatically configured to maintain the necessary closure pressure (about 3 kg/cm² to about 16 kg/cm²) between the opposing jaw members 110 and 120, respectively, to effect sealing. It is known that over pressurizing the jaw members may lead to ineffective tissue sealing.

It is envisioned that by making the forceps 10 disposable, the forceps 10 is less likely to become damaged since it is only intended for a single use and, therefore, does not require cleaning or re-sterilization. As a result, the functionality and consistency of the vital sealing components, e.g., the conductive surfaces 112 and 122, the stop member(s) 175, and the insulative housings 126 and 116 will assure a uniform and quality seal.

FIGS. 3 and 4 show the electrical details relating to the switch 50. More particularly and as mentioned above, cable 70 includes three electrical leads 71a, 71b and 71c which are fed through shaft 12b. The electrosurgical cable 70 is fed into the bottom of shaft 12b and is held securely therein by one or more mechanical interfaces (not shown). Lead 71c extends directly from cable 70 and connects to jaw member 120 to conduct the second electrical potential thereto. Leads 71a and 71b extend from cable 70 and connect to a circuit board 52.

Several different types of handswitches 50 are envisioned, for example, switch 50 is a regular push-button style switch but may be configured more like a toggle switch which permits the user to selectively activate the forceps 10 in a variety of different orientations, i.e., multi-oriented activation, which simplifies activation. One particular type of handswitch is disclosed in commonly-owned, co-pending U.S. patent application Ser. No. 10/460,926 the contents of which are hereby incorporated by reference herein.

The electrical leads 71a and 71b are electrically connected to the circuit board 52 such that when the switch 50 is depressed, a trigger lead 72 carries the first electrical potential from the circuit board 52 to jaw member 110. As mentioned above, the second electrical potential is carried by lead 71c directly from the generator (not shown) to jaw member 120 through the terminal connector 150 as described above. It is envisioned that a safety switch or circuit (not shown) may be employed such that the switch 50 cannot fire unless the jaw members 110 and 120 are closed and/or unless the jaw members 110 and 120 have tissue 400 held therebetween. In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 the entire contents of which are hereby incorporated by reference herein.

Figure 2A:
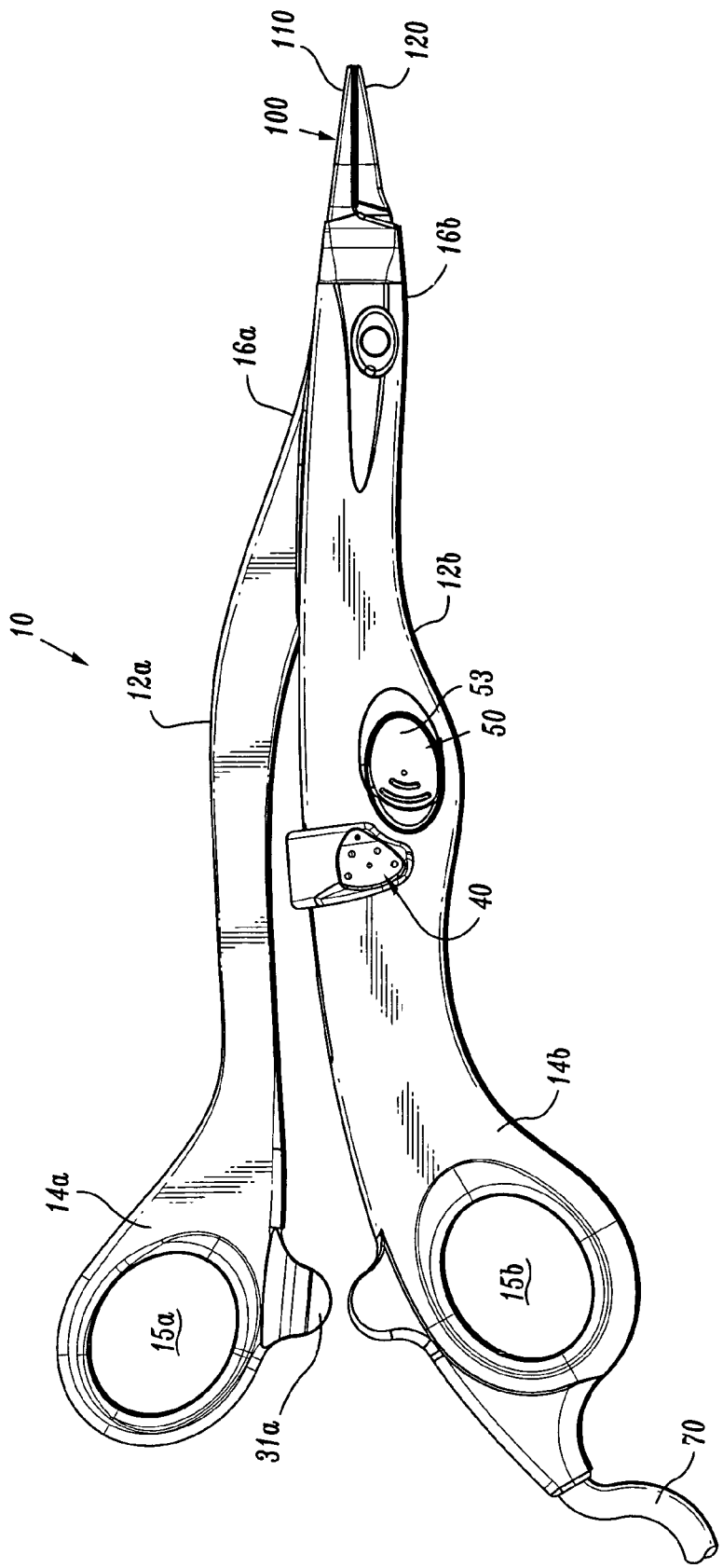
FIG. 2A is a left, side view of the forceps of FIG. 1A.
Figure 2C:
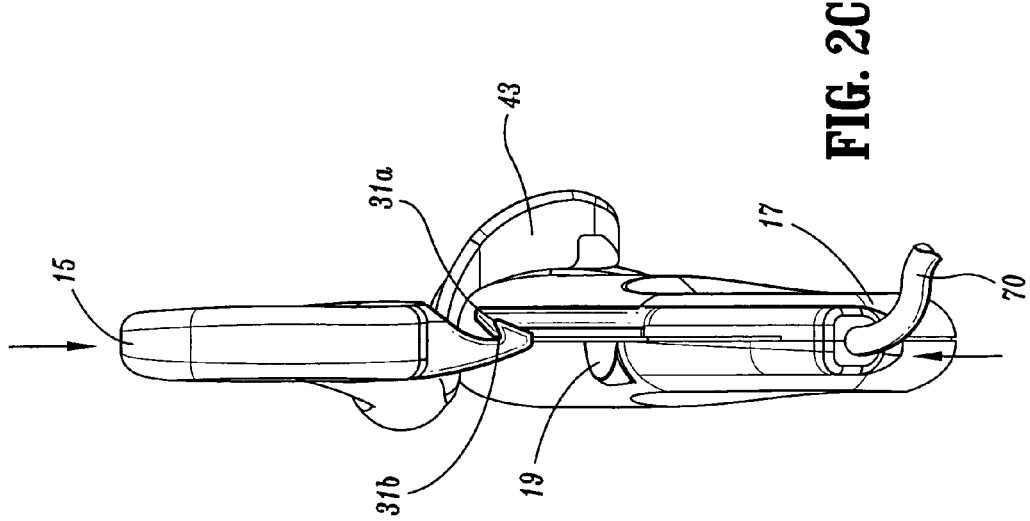
FIG. 2C is a rear view of the forceps shown in FIG. 1C.
Figure 2B:
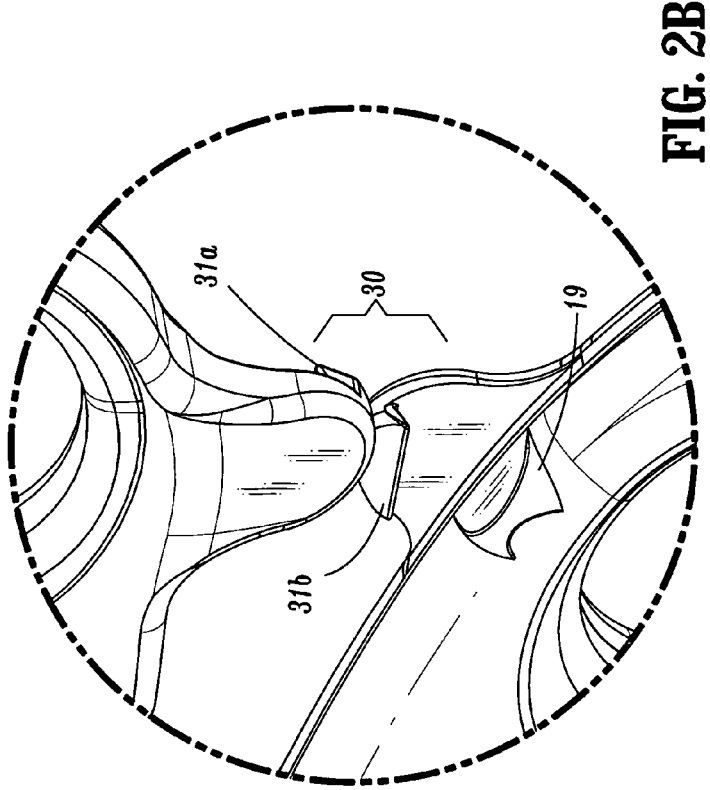
FIG. 2B is an enlarged view of the area of detail of FIG. 1B.
Figure 5:
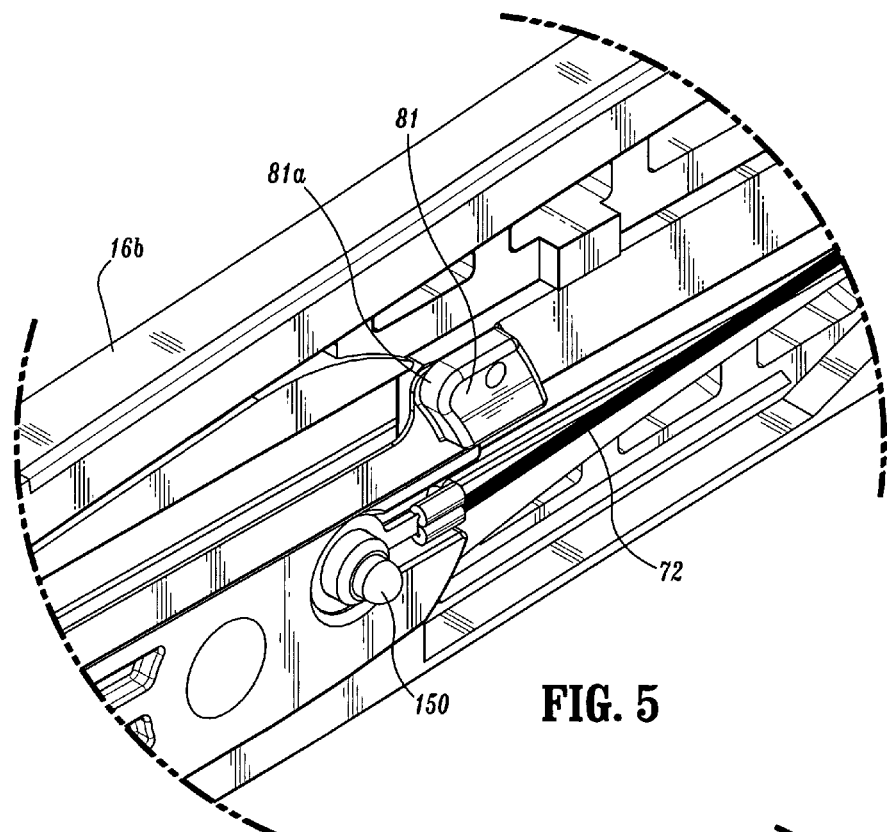
FIG. 5 is an enlarged, perspective view showing the area of detail in FIG. 3.
Figure 6:
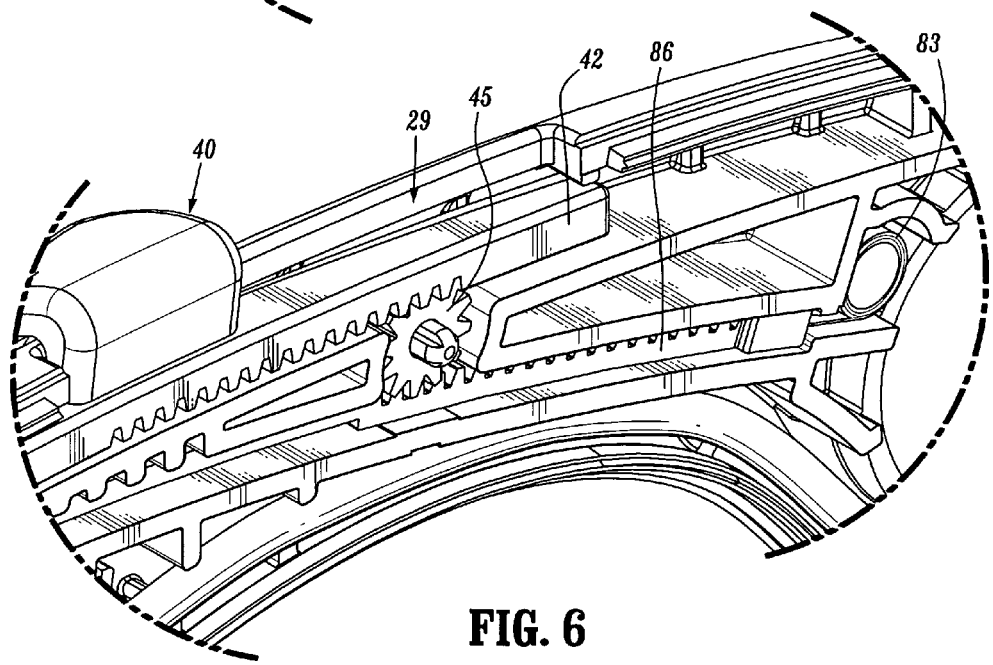
FIG. 6 is an enlarged, perspective view showing the area of detail in FIG. 3.

As best shown in FIGS. 1A, 2A and 7A, a switch cap 53 is positioned in electromechanical communication with the circuit board 52 along one side of shaft 12b to facilitate activation of switch 50. As can be appreciated, the position of the switch cap 53 enables the user to easily and selectively energize the jaw members 110 and 120 with a single hand. It is envisioned that the switch cap 53 may be hermetically-sealed to avoid damage to the circuit board 52 during wet operating conditions. In addition, it is contemplated that by positioning the switch cap 53 at a point distal to the actuating assembly 40, the overall sealing process is greatly simplified and ergonomically advantageous to the surgeon, i.e., after activation, the surgeon's finger is automatically poised for actuation of the actuating assembly 40 to advance the cutting mechanism 80. The geometry also disallows inadvertent actuation of the forceps 10 when the forceps 10 is not activated or "powered down".

The jaw members 110 and 120 are electrically isolated from one another such that electrosurgical energy can be effectively transferred through the tissue to form a tissue seal. Preferably, each jaw member, e.g., 110, includes a uniquely-designed electrosurgical cable path disposed therethrough which transmits electrosurgical energy to the electrically conductive sealing surface 112. It is envisioned that the jaw members 110 and 120 may include one or more cable guides or crimp-like electrical connectors to direct the cable leads towards electrically conductive sealing surfaces 112 and 122. Preferably, cable leads are held securely along the cable path to permit pivoting of the jaw members 110 and 120 about pivot 65.

As best shown in FIG. 7A, the cable leads 71a, 71b and 71c are protected by two insulative layers, an outer protective sheath which surrounds all three leads 71a, 71b and 71c and a secondary protective sheath which surrounds each individual cable lead, 71a, 71b and 71c, respectively. The two electrical potentials are isolated from one another by virtue of the insulative sheathing surrounding each cable lead 71a, 71b and 71c.

Figure 21:
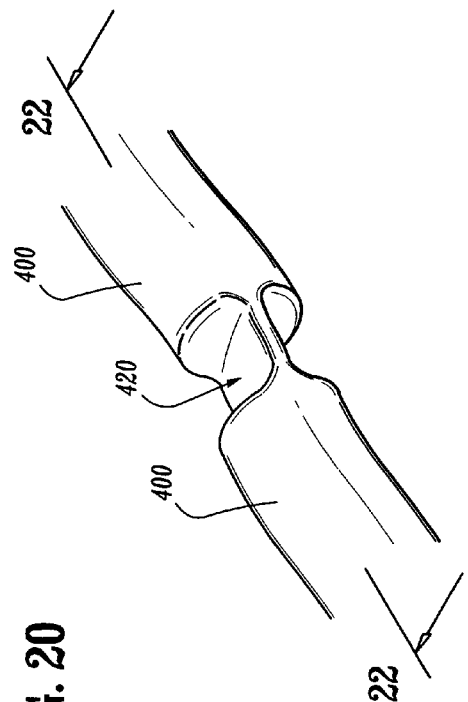
FIG. 21 is a greatly-enlarged, perspective view of a tissue seal.
Figure 22:
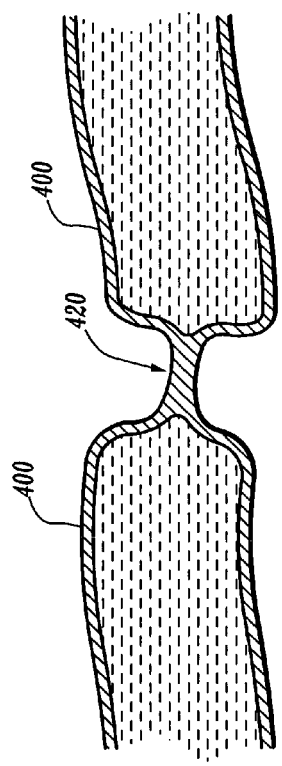
FIG. 22 is a side cross sectional view taken along line 22-22 of FIG. 21.
Figure 25:
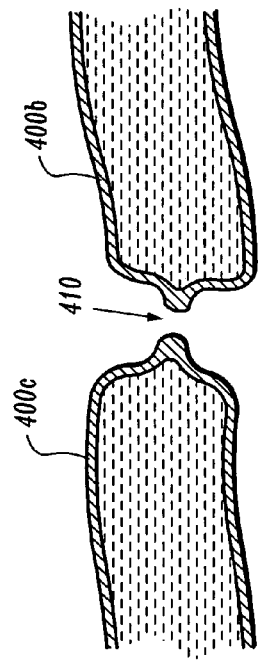
FIG. 25 is a greatly-enlarged, cross sectional view showing tissue separated along the tissue seal after advancement of the cutting mechanism.

In operation, the surgeon simply utilizes the two opposing handle members 15 and 17 to grasp tissue between jaw members 110 and 120. The surgeon then activates the handswitch 50 to provide electrosurgical energy to each jaw member 110 and 120 to communicate energy through the tissue held therebetween to effect a tissue seal (See FIGS. 21 and 22). Once sealed, the surgeon activates the actuating mechanism 40 to advance the cutting blade 87 through the tissue to sever the tissue 400 along the tissue seal (See FIG. 25).

From the foregoing and with reference to the various figure drawings, those skilled in the art will appreciate that certain modifications can also be made to the present disclosure without departing from the scope of the same. For example, although the electrical connections are preferably incorporated within one shaft 12b and the forceps 10 is intended for right-handed use, it is contemplated the electrical connections may be incorporated within the other shaft 12a depending upon a particular purpose and/or to facilitate manipulation by a left-handed user. Alternatively, the forceps 10 may operated in an upside down orientation for left-handed users without compromising or restricting any operating characteristics of the forceps 10.

It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120. Commonly-owned U.S. patent application Ser. No. 10/427,832 discloses several different types of sensory feedback mechanisms and algorithms which may be utilized for this purpose. The contents of this application are hereby incorporated by reference herein.

Experimental results suggest that the magnitude of pressure exerted on the tissue by the sealing surfaces of the jaw members 110 and 120 is important in assuring a proper surgical outcome. Tissue pressures within a working range of about 3 kg/cm² to about 16 kg/cm² and, preferably, within a working range of 7 kg/cm² to 13 kg/cm² have been shown to be effective for sealing arteries and vascular bundles. Tissue pressures within the range of about 4 kg/cm² to about 10 kg/cm² have proven to be particularly effective in sealing arteries and tissue bundles. Preferably, the inter-engaging surfaces 31a and 31b of the ratchet 30 are positioned to provide a closure within this working range. In addition and if the ratchet 30 includes multiple positions as explained above, it is envisioned that each particular ratchet position employs a specific closure force on tissue for particular surgical purposes. For example, the shafts 12a and 12b may be manufactured such that the spring constants of the shaft portions 12a and 12b, in conjunction with the placement of the ratchet interfaces 31a and 31b, will yield pressures within the above working range. If desired, the forceps 10 may be manufactured to include successive ratchet positions, i.e., ratchet interfaces 21a and 31b which would increase the closure force between opposing sealing surfaces 112 and 122 incrementally within the above working range or, if desired, outside the working range to suit a particular surgical purpose.

It is also envisioned that the drive rod 89 may be connected to the same or alternate source of electrosurgical energy and may be selectively energizable by the surgeon during cutting. As can be appreciated, this would enable the surgeon to electrosurgically cut the tissue along the tissue seal. As a result thereof, a substantially dull blade may be employed to electrosurgically cut the tissue. It is also envisioned that a substantially dull blade may be utilized with a spring loaded non-electrically energized cutting mechanism which, due to the clamping pressure between the opposing jaw members 110 and 120 and due to the force at which the spring-loaded cutting mechanism advances the blade, the tissue will sever along the tissue seal.

It is also contemplated that the forceps may include a safety blade return mechanism (not shown). For example and as mentioned above, the cutting blade 80 may include one or more springs which automatically return the cutting blade 87 after actuation of the actuator 40. In addition, a manual return may be included which allows the user to manually return the blade 87 if the automatic blade return (e.g., spring) should fail due to sticking, skewing, or some other unforeseen surgical condition. Alternatively, the actuating mechanism 40 may be spring-loaded and advanced automatically when tab 43 is depressed by the surgeon. After deployment, the surgeon manually retracts the tab 43 to reset the tab 43 and cutting mechanism 80 for subsequent deployment.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An open electrosurgical forceps for sealing tissue, comprising:
    a pair of first and second shaft members each having a jaw member disposed at a distal end thereof, the jaw members being movable from a first position in spaced relation relative to one another to at least one subsequent position wherein the jaw members cooperate to grasp tissue therebetween;
    each of the jaw members including an electrically conductive sealing plate for communicating electrosurgical energy through tissue held therebetween;
    at least one of the jaw members including a knife channel defined along a length thereof, the knife channel being dimensioned to reciprocate a cutting mechanism therealong; and
    an actuator operatively connected to one of the shaft members for selectively advancing the cutting mechanism from a first position wherein the cutting mechanism is disposed proximal to tissue held between the jaw members to at least one subsequent position wherein the cutting mechanism is disposed distal to tissue held between the jaw members; and
    a safety lockout to prevent reciprocation of the cutting mechanism when the jaw members are disposed in the first position, the safety lockout forming part of at least one of the jaw members.

2. An open electrosurgical forceps for sealing tissue according to claim 1 wherein the actuator includes a rack and pinion system having:
    a first gear-like rack connected to a trigger;
    a second gear-like rack connected to the cutting mechanism; and
    a pinion disposed between the first and second racks.

* * * * *